United States Patent
Reich et al.

(10) Patent No.: US 8,193,163 B2
(45) Date of Patent: Jun. 5, 2012

(54) COMPOSITIONS AND METHODS FOR SIRNA INHIBITION OF ICAM-1

(75) Inventors: Samuel J. Reich, Miami Beach, FL (US); Michael J. Tolentino, Lakeland, FL (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/952,046

(22) Filed: Nov. 22, 2010

(65) Prior Publication Data
US 2011/0092571 A1    Apr. 21, 2011

Related U.S. Application Data

(63) Continuation of application No. 12/329,221, filed on Dec. 5, 2008, now Pat. No. 7,847,090, which is a continuation of application No. 10/759,878, filed on Jan. 16, 2004, now abandoned.

(60) Provisional application No. 60/440,579, filed on Jan. 16, 2003.

(51) Int. Cl.
- C07H 21/02    (2006.01)
- C07H 21/04    (2006.01)
- C12Q 1/68    (2006.01)
- C12P 19/34    (2006.01)
- C01N 43/04    (2006.01)
- C12N 5/00    (2006.01)
- C12N 5/02    (2006.01)

(52) U.S. Cl. ....... 514/44; 536/23.1; 536/24.1; 536/24.3; 536/24.5; 435/6; 435/91.1; 435/325; 435/375

(58) Field of Classification Search ............... 536/23.1, 536/24.3, 24.33, 24.5; 514/44
See application file for complete search history.

(56) References Cited

U.S. PATENT DOCUMENTS

| | | | |
|---|---|---|---|
| 6,015,894 | A | 1/2000 | Bennett et al. |
| 6,096,722 | A | 8/2000 | Bennett et al. |
| 6,177,401 | B1 | 1/2001 | Ullrich et al. |
| 6,506,559 | B1 | 1/2003 | Driver et al. |
| 7,195,916 | B2 | 3/2007 | Qin et al. |
| 2002/0086356 | A1 | 7/2002 | Tuschl et al. |
| 2002/0132788 | A1 | 9/2002 | Lewis et al. |
| 2002/0162126 | A1 | 10/2002 | Beach et al. |
| 2002/0173478 | A1 | 11/2002 | Gewirtz |
| 2004/0220129 | A1 | 11/2004 | Reich et al. |
| 2005/0048529 | A1 | 3/2005 | McSwiggen |
| 2005/0187174 | A1 | 8/2005 | Richards et al. |

FOREIGN PATENT DOCUMENTS

| | | |
|---|---|---|
| CA | 2351980 | 6/2007 |
| WO | WO99/54341 A1 | 10/1999 |
| WO | WO02/44321 A2 | 6/2002 |

(Continued)

OTHER PUBLICATIONS

Agami, RNAi and related mechanisms and thier potential use for therapy, *Curr Opin Chem Biol.* (Dec. 2002), (6):829-834.

(Continued)

*Primary Examiner* — Terra Cotta Gibbs
(74) *Attorney, Agent, or Firm* — Pepper Hamilton LLP

(57) ABSTRACT

RNA interference using small interfering RNAs which are specific for the ICAM-1 gene inhibits expression of this gene. Diseases which involve ICAM-1-mediated cell adhesion, such as inflammatory and autoimmune diseases, diabetic retinopathy and other complications arising from type I diabetes, age related macular degeneration and many types of cancer, can be treated by administering the small interfering RNAs.

77 Claims, 3 Drawing Sheets

FOREIGN PATENT DOCUMENTS

WO    WO03/099298 A1    12/2003

OTHER PUBLICATIONS

Agrawal, et al., Anitsense therapeutics: is it as simple as complementary base recognition?, *Mol Med Today* (Feb. 2000), 6(2):72-81.

Bennett, et al., Humoral response after administration of E1-deleted adenoviruses: immune privilege of the subretinal space, *Hum Gene Ther.* (Sep. 10, 1996), 7(14): 1763-1769.

Caplen, RNAi as a gene therapy approach, *Expert Opin Bio Ther.* (Jul. 2003), 3(4):575- 586.

Coburn, et al., siRNAs: a new waive of RNA-based therapeutics, *Antimicrob Chemother.* (Apr.2003), 51(4):753-756.

Devroe, et al., Retrovirus-delivered siRNA, *BMC Biotechnology* (Aug. 28,:2002), 1-5.

Diallo, et al., Long endogenous dsRNAs can induce complete gene silencing in mammalian cells and primary cultures, *Oligonucleotides* (2003), 13(5):381-392.

Downward, et al., RNA interference, *BMJ* (May 22, 2004),328(7450):1245-1248.

Dragun, et al., ICAM-1 antisense oligodesoxynucleotides prevent reperfusion injury and enhance immediate graft function in renal transplantation, *Kidney Int.* (Aug. 1998),54(2):590-602.

Elbashir, et al., RNA interference is mediated by 21- and 22-nucleotide RNAs, *Genes. Dev.* (Jan. 15, 2001),15(2):188-200.

Elbashir, et al., Duplexes of 21- nucleotide RNAs mediate RNA interference in cultured mammalian cells, *Nature* (May 24, 2001),411(6836):494-498.

Erickson, RNAi Revs up, *Start-Up* (Oct. 2002),1-12.

Fire, et al., Potent and specific genetic interference by double-stranded RNA in Caenorhabditis elegans, *Nature* (Feb. 19, 1998),391(6669):806-811.

FJose, et al., RNAi and microRNAs: from animal models to disease therapy, *Birth Defects Res C Embryo Today* (Jun. 2006),78(2):150-171.

Hammond, et al., Post-transcriptional gene silencing by double-stranded RNA, *Nat Rev Genet* ,(Feb. 2001),2(2):110-119. .

Holash, et. al., VEGF-Trap: a VEGF blocker with potential antitumor effects, *Proc Natl Acad Sci USA* (Aug. 20, 2002),99(17):11393-11398.

Jen, et al., Suppression of gene expression by targeted disruption of messenger RNA: available options and current strategies, *Stem Cells* (2000),18(5):307-319.

Katz, et al., ICAM-1 antisense oligodeoxynucleotide improves islet allograft survival and function, *Cell Transplant* (Nov.-Dec. 2000),9(6):817-828.

Kim, et al., Potent CEGF blockade causes regression of coopted vessels in a model of neuroblastoma, *Proc Natl Acad USA* (Aug. 20, 2002),99(17):11399-11404.

Ktetschmer-Kazemi, et al., The activity of siRNA in mammalian cells is related to structural target accessbility: a comparison with antisense oligonueleotides, *Nucleic Acids Res.* (Aug. 1, 2003),31(15):4417-1424.

Lu, et al., RNA Interference Technology: From Basic Science to Drug Development—Delivering siRNA in vivo for functional genomics and novel therapeutics, Published by the Press Syndicate of The University of Cambridge, United Kingdom,(2005),303-317.

Miyamoto, et al., Vascular endothelial growth factor (VEGF)-induced retinal vascular permeability is mediated by intercellular adhesion molecule-1 (ICAM-1), *Am J Pathol.* (May 2000),156(5):1733-1739.

Miyamoto, et al., Prevention of leukostasis and vascular leakage in streptozotocin-induced diabetic retinopathy via intercellular adhesion molecule~1 inhibition, *Proc Natl Acad Sci USA* (Sep. 14, 1999),96(19):10836-10841.

Moromizato, et al., CD18 and ICAM~1~dependent corneal neovascularization and inflammation after limbal injury, *Am J Pathol.* (Oct. 2000),157(4):1277-1281.

Nishiwaki, et at., Introduction of short interfering RNA to silence endogenous E-selectin in vascular endothelium leads to successful inhibition of leukocyte adhesion, *Biochem Biophys Res Commun.* (Oct. 31, 2003),310(4):1062-1066.

Novina, et al., siRNA-directed inhibition of HIV-1 infection, *Nat Med.* (Jul. 2002),8(7);681-686.

Paroo, et at., Challenges for RNAi in vivo, *Trends Biotechnol.* (Aug. 2004),22(8):390- 394.

Rose, et al., Functional polarity is introduced by Dicer processing of short substrate RNAs, *Nucleic Acids Res.* (Jul. 26, 2005), 33(13):4140-4156.

Sakurai, et al., Targeted Disruption of the CD18 or ICAM-1 gene inhibits choroidal neovascularization, *Invest Ophthalmol Vis Sci.* (Jun. 2003),44(6):2743-2749.

Samarsky, et al., RNA Interference Technology: From Basic Science to Drug Development—RNAi in drug development: Practical considerations, Published by the Press Syndicate of The University of Cambridge, United Kingdom,(2005),384-395.

Shu, et al., Sphingosine kinase mediates vascular endothelial growth factor-induced activation of Ras and mitogen-activated protein kinases, *Mol Cell Biol.* (Nov. 2002),22(22):7758-7768.

Tischer, et al., The human gene for vascular endothelial growth factor, Multiple protein forms are encoded through alternative exon splicing, *J Biol Chem.* (Jun. 25, 1991),266(18):11947-11954.

Tuschi., The siRNA user guide: Selection of siRNA duplexes from the target mRNA sequence, www.mpibpc.gwdg.de/abteilungen/100/105.sirna.html (revised Oct. 11, 2002).

Tuschl, Expanding Small RNA Interference, *Nat Biotechnol.* (May 2002),20(5):446-448.

Van Brunt, Signals: The online magazine of Biotechnology Industry Analysis, Shoot the Messenger, www.signalsmag.com/signalsmag.../3DF5AEF6049C99256C1D0055BAA (Aug. 22, 2002).

Vickers, et al., Efficient reduction of target RNAs by small interfering RNA and RNase H-dependent antisense agents. A comparative analysis, *J Biol Chem.* (Feb. 28, 2002),278(9):7108-7118.

Warren, Successful ICAM-1 gene inactivation in plurlpotent stem cells using RNA interference and in site expressed antisense/ribozyme transgenes, *J Am Soc Nephrol.* (2002)(Abstract).

Xia, et al., siRNA-mediated gene silencing in vitro and in vivo, *Nat Biotechnol.* (Oct. 2002),20(10):1006-1010.

SEQUENCE LISTING

<160> NUMBER OF SEQ ID NOS: 94

<210> SEQ ID NO 1
<211> LENGTH: 2900
<212> TYPE: DNA
<213> ORGANISM: Homo sapiens

<400> SEQUENCE: 1

| | | |
|---|---|---|
| gcgccccagt cgacgctgag ctcctctgct actcagagtt gcaacctcag cctcgctatg | 60 |
| gctcccagca gcccccggcc cgcgctgccc gcactcctgg tcctgctcgg ggctctgttc | 120 |
| ccaggacctg gcaatgccca gacatctgtg tcccccctcaa aagtcatcct gccccgggga | 180 |
| ggctccgtgc tggtgacatg cagcacctcc tgtgaccagc ccaagttgtt gggcatagag | 240 |
| accccgttgc taaaaaggaa gttgctcctg cctgggaaca accggaaggt gtatgaactg | 300 |
| agcaatgtgc aagaagatag ccaaccaatg tgctattcaa actgccctga tgggcagtca | 360 |
| acagctaaaa ccttcctcac cgtgtactgg actccagaac gggtggaact ggcacccctc | 420 |
| ccctcttggc agccagtggg caagaacctt accctacgct gccaggtgga gggtgggca | 480 |
| ccccgggcca acctcaccgt ggtgctgctc cgtggggaga aggagctgaa acgggagcca | 540 |
| gctgtggggg agcccgctga ggtcacgacc acgqtgctgg tgaggagaga tcaccatgga | 600 |
| gccaatttct cgtgccgcac tgaactggac ctgcggcccc aagggctgga gctgtttgag | 660 |
| aacacctcgg ccccctacca gctccagacc tttgtcctgc cagcgactcc cccacaactt | 720 |
| gtcagccccc gggtcctaga ggtggacacg cagggggaccg tggtctgttc cctggacggg | 780 |
| ctgttcccag tctcggaggc ccaggtccac ctggcactgg gggaccagag gttgaacccc | 840 |
| acagtcacct atggcaacga ctccttctcg gccaaggcct cagtcagtgt gaccgcagag | 900 |
| gacgagggca cccagcggct gacgtgtgca gtaatactgg ggaaccagag ccaggagaca | 960 |
| ctgcagacag tgaccatcta cagctttccg gcgcccaacg tgattctgac gaagccagag | 1020 |
| gtctcagaag ggaccgaggt gacagtgaag tgtgaggccc acccaagagc caaggtgacg | 1080 |
| ctgaatgggg ttccagccca gccactgggc cgaggqcc agctcctgct gaaggccacc | 1140 |
| ccagaggaca acgggcgcag cttctcctgc tctgcaaccc tggaggtggc cggccagctt | 1200 |
| atacacaaga accagacccg ggagcttcgt gtcctgtatg cccccgact ggacgagagg | 1260 |
| gattgtccgg gaaactggac gtggccagaa aattcccagc agactccaat gtgccaggct | 1320 |
| tgggggaacc cattgcccga gctcaagtgt ctaaaggatg gcactttccc actgcccatc | 1380 |
| ggggaatcag tgactgtcac tcgagatctt gagggcacct acctctgtcg ggccaggagc | 1440 |
| actcaagggg aggtcacccg caaggtgacc gtgaatgtgc tctcccccg gtatgagatt | 1500 |
| gtcatcatca ctgtggtagc agccgcagtc ataatgggca ctgcaggcct cagcacgtac | 1560 |
| ctctataacc gccagcggaa gatcaagaaa tacagactac aacaggccca aaaagggac | 1620 |
| cccatgaaac cgaacacaca agccacgcct ccctgaacct atcccgggac agggcctctt | 1680 |
| cctcggcctt cccatattgg tggcagtggt gccacactga acagagtgga agacatatgc | 1740 |
| catgcagcta cacctaccgg ccctgggacg ccggaggaca gggcattgtc ctcagtcaga | 1800 |
| tacaacagca tttggggccc atctgatctg tagtcacatg actaagccaa gaggaaggag | 1860 |
| caagactcaa gacatgattg atggatgtta aagtctagcc tgatgagagg ggaagtggtg | 1920 |
| ggggagacat agccccacca tgaggacata caactgggaa atactgaaac ttgctgccta | 1980 |
| ttgggtatgc tgaggcccca cagacttaca gaagaagtgg ccctccatag acatggcact | 2040 |

-continued

```
gctgtctact gaccccaacc cttgatgata tgtatttatt catttgttat tttaccagct    2100
atttattgag tgtcttttat gtaggctaaa tgaacatagg tctctggcct cacggagctc    2160
ccagtcctaa tcacattcaa ggtcaccagg tacagttgta caggttgtac actgcaggag    2220
agtgcctggc aaaaagatca aatggggctg ggacttctca ttggccaacc tgcctttccc    2280
cagaaggagt gattttcta tcggcacaaa agcactatat ggactggtaa tggttacagg    2340
ttcagagatt acccagtgag gccttattcc tcccttcccc ccaaaactga cacctttgtt    2400
agccacctcc ccacccacat acatttctgc cagtgttcac aatgacactc agcggtcatg    2460
tctggacatg agtgcccagg gaatatgccc aagctatgcc ttgtcctctt gtcctgtttg    2520
catttcactg ggagcttgca ctatgcagct ccagtttcct gcagtgatca gggtcctgca    2580
agcagtgggg aagggggcca aggtattgga ggactccctc ccagctttgg aagcctcatc    2640
cgcgtgtgtg tgtgtgtgta tgtgtagaca agctctcgct ctgtcaccca ggctggagtg    2700
cagtggtgca atcatggttc actgcagtct tgaccttttg ggctcaagtg atcctcccac    2760
ctcagcctcc tgagtagctg gaccatagg ctcacaacac cacacctggc aaatttgatt     2820
ttttttttt ttccagagac ggggtctcgc aacattgccc agacttcctt tgtgttagtt     2880
aataaagctt tctcaactgc                                                2900
```

```
<210> SEQ ID NO 2
<211> LENGTH: 1614
<212> TYPE: DNA
<213> ORGANISM: Mus musculus

<400> SEQUENCE: 2
```

```
atggcttcaa cccgtgccaa gcccacgcta cctctgctcc tggccctggt caccgttgtg      60
atccctgggc ctggtgatgc tcaggtatcc atccatccca gagaagcctt cctgccccag     120
ggtgggtccg tgcaggtgaa ctgttcttcc tcatgcaagg aggacctcag cctgggcttg     180
gagactcagt ggctgaaaga tgagctcgag agtggaccca ctggaagct gtttgagctg     240
agcgagatcg ggaggacag cagtccgctg tgctttgaga actgtggcac cgtgcagtcg     300
tccgcttccg ctaccatcac cgtgtattcg tttccggaga gtgtggagct gagacctctg     360
ccagcctggc agcaagtagg caaggacctc accctgcgct gccacgtgga tggtggagca     420
ccgcggaccc agctctcagc agtgctgctc cgtggggagg agatactgag ccgccagcca     480
gtgggtgggc accccaagga ccccaaggag atcacattca cggtgctggc tagcagaggg     540
gaccacggag ccaatttctc atgccgcaca gaactggatc tcaggccgca agggctggca     600
tgttctctcta atgtctccga ggccaggagc ctccggactt tcgatcttcc agctaccatc     660
ccaaagctcg acacccctga cctcctggag gtgggcaccc agcagaagtt gttttgctcc     720
ctggaaggcc tgtttcctgc ctctgaagct cggatatacc tggagctggg aggccagatg     780
ccgacccagg agagcacaaa cagcagtgac tctgtgtcag ccactgcctt ggtagaggtg     840
actgaggagt tcgacagaac cctgccgctg cgctgcgttt tggagctagc ggaccagatc     900
ctggagacgc agaggacctt aacagtctac aactttcag ctccggtcct gaccctgagc      960
cagctggagg tctcggaagg gagccaagta actgtgaagt gtgaagccca cagtgggtcg    1020
aaggtggttc ttctgagcgg cgtcgagcct aggccaccca ccccgcaggt ccaattcaca    1080
ctgaatgcca gctcggagga tcacaaacga agcttctttt gctctgccgc tctggaggtg    1140
gcgggaaagt tcctgttaa aaaccagacc ctggaactgc acgtgctgta tggtcctcgg    1200
ctggacgaga cggactgctt gggaactgg acctggcaag aggggtctca gcagactctg    1260
```

|         |         |         |         |         |      |
|---------|---------|---------|---------|---------|------|
| aaatgccagg | cctgggggaa | cccatctcct | aagatgacct | gcagacggaa ggcagatggt | 1320 |
| gccctgctgc | ccatcggggt | ggtgaagtct | gtcaaacagg | agatgaatgg tacatacgtg | 1380 |
| tgccatgcct | ttagctccca | tgggaatgtc | accaggaatg | tgtacctgac agtactgtac | 1440 |
| cactctcaaa | ataactggac | tataatcatt | ctggtgccag | tactgctggt cattgtgggc | 1500 |
| ctcgtgatgg | cagcctctta | tgtttataac | cgccagagaa | agatcaggat atacaagtta | 1560 |
| cagaaggctc | aggaggaggc | cataaaactc | aagggacaag | ccccacctcc ctga | 1614 |

```
<210> SEQ ID NO 3
<211> LENGTH: 19
<212> TYPE: DNA
<213> ORGANISM: Artificial Sequence
<220> FEATURE:
<223> OTHER INFORMATION: target sequence

<400> SEQUENCE: 3
gttgttgggc atagagacc                                                     19

<210> SEQ ID NO 4
<211> LENGTH: 21
<212> TYPE: RNA
<213> ORGANISM: Artificial Sequence
<220> FEATURE:
<223> OTHER INFORMATION: siRNA sense strand

<400> SEQUENCE: 4
guuguugggc auagagaccu u                                                  21

<210> SEQ ID NO 5
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 5
ggucucuaug cccaacaacu u                                                  21

<210> SEQ ID NO 6
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_RNA
<222> LOCATION: (1)...(19)
<223> OTHER INFORMATION: ribonucleotide bases

<400> SEQUENCE: 6
guuguugggc auagagacct t                                                  21

<210> SEQ ID NO 7
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_RNA
<222> LOCATION: (1)...(19)
<223> OTHER INFORMATION: ribonucleotide bases

<400> SEQUENCE: 7
ggucucuaug cccaacaact t                                                  21
```

```
<210> SEQ ID NO 8
<211> LENGTH: 19
<212> TYPE: DNA
<213> ORGANISM: Artificial Sequence
<220> FEATURE:
<223> OTHER INFORMATION: target sequence

<400> SEQUENCE: 8
ggagttgctc ctgcctggg                                              19

<210> SEQ ID NO 9
<211> LENGTH: 19
<212> TYPE: DNA
<213> ORGANISM: Artificial Sequence
<220> FEATURE:
<223> OTHER INFORMATION: target sequence

<400> SEQUENCE: 9
ccggaaggtg tatgaactg                                              19

<210> SEQ ID NO 10
<211> LENGTH: 19
<212> TYPE: DNA
<213> ORGANISM: Artificial Sequence
<220> FEATURE:
<223> OTHER INFORMATION: target sequence

<400> SEQUENCE: 10
ctgagcaatg tgcaagaag                                              19

<210> SEQ ID NO 11
<211> LENGTH: 19
<212> TYPE: DNA
<213> ORGANISM: Artificial Sequence
<220> FEATURE:
<223> OTHER INFORMATION: target sequence

<400> SEQUENCE: 11
tgtgctattc aaactgccc                                              19

<210> SEQ ID NO 12
<211> LENGTH: 19
<212> TYPE: DNA
<213> ORGANISM: Artificial Sequence
<220> FEATURE:
<223> OTHER INFORMATION: target sequence

<400> SEQUENCE: 12
ccttcctcac cgtgtactg                                              19

<210> SEQ ID NO 13
<211> LENGTH: 19
<212> TYPE: DNA
<213> ORGANISM: Artificial Sequence
<220> FEATURE:
<223> OTHER INFORMATION: target sequence

<400> SEQUENCE: 13
cgggtggaac tggcacccc                                              19

<210> SEQ ID NO 14
<211> LENGTH: 19
<212> TYPE: DNA
<213> ORGANISM: Artificial Sequence
<220> FEATURE:
<223> OTHER INFORMATION: target sequence
```

```
<400> SEQUENCE: 14
ccttacccta cgctgccag                                                    19

<210> SEQ ID NO 15
<211> LENGTH: 19
<212> TYPE: DNA
<213> ORGANISM: Artificial Sequence
<220> FEATURE:
<223> OTHER INFORMATION: target sequence

<400> SEQUENCE: 15
cctcaccgtg gtgctgctc                                                    19

<210> SEQ ID NO 16
<211> LENGTH: 19
<212> TYPE: DNA
<213> ORGANISM: Artificial Sequence
<220> FEATURE:
<223> OTHER INFORMATION: target sequence

<400> SEQUENCE: 16
cgggagccag ctgtgggggg                                                   19

<210> SEQ ID NO 17
<211> LENGTH: 19
<212> TYPE: DNA
<213> ORGANISM: Artificial Sequence
<220> FEATURE:
<223> OTHER INFORMATION: target sequence

<400> SEQUENCE: 17
tttctcgtgc cgcactgaa                                                    19

<210> SEQ ID NO 18
<211> LENGTH: 19
<212> TYPE: DNA
<213> ORGANISM: Artificial Sequence
<220> FEATURE:
<223> OTHER INFORMATION: target sequence

<400> SEQUENCE: 18
ctggacctgc ggccccaag                                                    19

<210> SEQ ID NO 19
<211> LENGTH: 19
<212> TYPE: DNA
<213> ORGANISM: Artificial Sequence
<220> FEATURE:
<223> OTHER INFORMATION: target sequence

<400> SEQUENCE: 19
ggcctcagtc agtgtgacc                                                    19

<210> SEQ ID NO 20
<211> LENGTH: 21
<212> TYPE: DNA
<213> ORGANISM: Artificial Sequence
<220> FEATURE:
<223> OTHER INFORMATION: target sequence

<400> SEQUENCE: 20
aatgcccaga catctgtgtc c                                                 21

<210> SEQ ID NO 21
<211> LENGTH: 21
<212> TYPE: DNA
```

```
<213> ORGANISM: Artificial Sequence
<220> FEATURE:
<223> OTHER INFORMATION: target sequence

<400> SEQUENCE: 21
aaaagtcatc ctgccccggg g                                              21

<210> SEQ ID NO 22
<211> LENGTH: 21
<212> TYPE: DNA
<213> ORGANISM: Artificial Sequence
<220> FEATURE:
<223> OTHER INFORMATION: target sequence

<400> SEQUENCE: 22
aaagtcatcc tgccccgggg a                                              21

<210> SEQ ID NO 23
<211> LENGTH: 21
<212> TYPE: DNA
<213> ORGANISM: Artificial Sequence
<220> FEATURE:
<223> OTHER INFORMATION: target sequence

<400> SEQUENCE: 23
aagtcatcct gccccgggga g                                              21

<210> SEQ ID NO 24
<211> LENGTH: 21
<212> TYPE: DNA
<213> ORGANISM: Artificial Sequence
<220> FEATURE:
<223> OTHER INFORMATION: target sequence

<400> SEQUENCE: 24
aagttgttgg gcatagagac c                                              21

<210> SEQ ID NO 25
<211> LENGTH: 21
<212> TYPE: DNA
<213> ORGANISM: Artificial Sequence
<220> FEATURE:
<223> OTHER INFORMATION: target sequence

<400> SEQUENCE: 25
aaaaaggagt tgctcctgcc t                                              21

<210> SEQ ID NO 26
<211> LENGTH: 21
<212> TYPE: DNA
<213> ORGANISM: Artificial Sequence
<220> FEATURE:
<223> OTHER INFORMATION: target sequence

<400> SEQUENCE: 26
aaaaggagtt gctcctgcct g                                              21

<210> SEQ ID NO 27
<211> LENGTH: 21
<212> TYPE: DNA
<213> ORGANISM: Artificial Sequence
<220> FEATURE:
<223> OTHER INFORMATION: target sequence

<400> SEQUENCE: 27
aaaggagttg ctcctgcctg g                                              21
```

<210> SEQ ID NO 28
<211> LENGTH: 21
<212> TYPE: DNA
<213> ORGANISM: Artificial Sequence
<220> FEATURE:
<223> OTHER INFORMATION: target sequence

<400> SEQUENCE: 28
aaggagttgc tcctgcctgg g                                             21

<210> SEQ ID NO 29
<211> LENGTH: 21
<212> TYPE: DNA
<213> ORGANISM: Artificial Sequence
<220> FEATURE:
<223> OTHER INFORMATION: target sequence

<400> SEQUENCE: 29
aacaaccgga aggtgtatga a                                             21

<210> SEQ ID NO 30
<211> LENGTH: 21
<212> TYPE: DNA
<213> ORGANISM: Artificial Sequence
<220> FEATURE:
<223> OTHER INFORMATION: target sequence

<400> SEQUENCE: 30
aaccggaagg tgtatgaact g                                             21

<210> SEQ ID NO 31
<211> LENGTH: 21
<212> TYPE: DNA
<213> ORGANISM: Artificial Sequence
<220> FEATURE:
<223> OTHER INFORMATION: target sequence

<400> SEQUENCE: 31
aaggtgtatg aactgagcaa t                                             21

<210> SEQ ID NO 32
<211> LENGTH: 21
<212> TYPE: DNA
<213> ORGANISM: Artificial Sequence
<220> FEATURE:
<223> OTHER INFORMATION: target sequence

<400> SEQUENCE: 32
aactgagcaa tgtgcaagaa g                                             21

<210> SEQ ID NO 33
<211> LENGTH: 21
<212> TYPE: DNA
<213> ORGANISM: Artificial Sequence
<220> FEATURE:
<223> OTHER INFORMATION: target sequence

<400> SEQUENCE: 33
aatgtgcaag aagatagcca a                                             21

<210> SEQ ID NO 34
<211> LENGTH: 21
<212> TYPE: DNA
<213> ORGANISM: Artificial Sequence
<220> FEATURE:
<223> OTHER INFORMATION: target sequence

```
<400> SEQUENCE: 34
aagaagatag ccaaccaatg t                                              21

<210> SEQ ID NO 35
<211> LENGTH: 21
<212> TYPE: DNA
<213> ORGANISM: Artificial Sequence
<220> FEATURE:
<223> OTHER INFORMATION: target sequence

<400> SEQUENCE: 35
aagatagcca accaatgtgc t                                              21

<210> SEQ ID NO 36
<211> LENGTH: 21
<212> TYPE: DNA
<213> ORGANISM: Artificial Sequence
<220> FEATURE:
<223> OTHER INFORMATION: target sequence

<400> SEQUENCE: 36
aaccaatgtg ctattcaaac t                                              21

<210> SEQ ID NO 37
<211> LENGTH: 21
<212> TYPE: DNA
<213> ORGANISM: Artificial Sequence
<220> FEATURE:
<223> OTHER INFORMATION: target sequence

<400> SEQUENCE: 37
aatgtgctat tcaaactgcc c                                              21

<210> SEQ ID NO 38
<211> LENGTH: 21
<212> TYPE: DNA
<213> ORGANISM: Artificial Sequence
<220> FEATURE:
<223> OTHER INFORMATION: target sequence

<400> SEQUENCE: 38
aaactgccct gatgggcagt c                                              21

<210> SEQ ID NO 39
<211> LENGTH: 21
<212> TYPE: DNA
<213> ORGANISM: Artificial Sequence
<220> FEATURE:
<223> OTHER INFORMATION: target sequence

<400> SEQUENCE: 39
aactgccctg atgggcagtc a                                              21

<210> SEQ ID NO 40
<211> LENGTH: 21
<212> TYPE: DNA
<213> ORGANISM: Artificial Sequence
<220> FEATURE:
<223> OTHER INFORMATION: target sequence

<400> SEQUENCE: 40
aacagctaaa accttcctca c                                              21

<210> SEQ ID NO 41
<211> LENGTH: 21
<212> TYPE: DNA
```

<213> ORGANISM: Artificial Sequence
<220> FEATURE:
<223> OTHER INFORMATION: target sequence

<400> SEQUENCE: 41
aaaaccttcc tcaccgtgta c                                              21

<210> SEQ ID NO 42
<211> LENGTH: 21
<212> TYPE: DNA
<213> ORGANISM: Artificial Sequence
<220> FEATURE:
<223> OTHER INFORMATION: target sequence

<400> SEQUENCE: 42
aaaccttcct caccgtgtac t                                              21

<210> SEQ ID NO 43
<211> LENGTH: 21
<212> TYPE: DNA
<213> ORGANISM: Artificial Sequence
<220> FEATURE:
<223> OTHER INFORMATION: target sequence

<400> SEQUENCE: 43
aaccttcctc accgtgtact g                                              21

<210> SEQ ID NO 44
<211> LENGTH: 21
<212> TYPE: DNA
<213> ORGANISM: Artificial Sequence
<220> FEATURE:
<223> OTHER INFORMATION: target sequence

<400> SEQUENCE: 44
aacgggtgga actggcaccc c                                              21

<210> SEQ ID NO 45
<211> LENGTH: 21
<212> TYPE: DNA
<213> ORGANISM: Artificial Sequence
<220> FEATURE:
<223> OTHER INFORMATION: target sequence

<400> SEQUENCE: 45
aactggcacc cctcccctct t                                              21

<210> SEQ ID NO 46
<211> LENGTH: 21
<212> TYPE: DNA
<213> ORGANISM: Artificial Sequence
<220> FEATURE:
<223> OTHER INFORMATION: target sequence

<400> SEQUENCE: 46
aagaacctta ccctacgctg c                                              21

<210> SEQ ID NO 47
<211> LENGTH: 21
<212> TYPE: DNA
<213> ORGANISM: Artificial Sequence
<220> FEATURE:
<223> OTHER INFORMATION: target sequence

<400> SEQUENCE: 47
aaccttaccc tacgctgcca g                                              21

<210> SEQ ID NO 48
<211> LENGTH: 21
<212> TYPE: DNA
<213> ORGANISM: Artificial Sequence
<220> FEATURE:
<223> OTHER INFORMATION: target sequence

<400> SEQUENCE: 48
aacctcaccg tggtgctgct c                                    21

<210> SEQ ID NO 49
<211> LENGTH: 21
<212> TYPE: DNA
<213> ORGANISM: Artificial Sequence
<220> FEATURE:
<223> OTHER INFORMATION: target sequence

<400> SEQUENCE: 49
aaggagctga acgggagcc a                                     21

<210> SEQ ID NO 50
<211> LENGTH: 21
<212> TYPE: DNA
<213> ORGANISM: Artificial Sequence
<220> FEATURE:
<223> OTHER INFORMATION: target sequence

<400> SEQUENCE: 50
aaacgggagc cagctgtggg g                                    21

<210> SEQ ID NO 51
<211> LENGTH: 21
<212> TYPE: DNA
<213> ORGANISM: Artificial Sequence
<220> FEATURE:
<223> OTHER INFORMATION: target sequence

<400> SEQUENCE: 51
aacgggagcc agctgtgggg g                                    21

<210> SEQ ID NO 52
<211> LENGTH: 21
<212> TYPE: DNA
<213> ORGANISM: Artificial Sequence
<220> FEATURE:
<223> OTHER INFORMATION: target sequence

<400> SEQUENCE: 52
aatttctcgt gccgcactga a                                    21

<210> SEQ ID NO 53
<211> LENGTH: 21
<212> TYPE: DNA
<213> ORGANISM: Artificial Sequence
<220> FEATURE:
<223> OTHER INFORMATION: target sequence

<400> SEQUENCE: 53
aactggacct gcggccccaa g                                    21

<210> SEQ ID NO 54
<211> LENGTH: 21
<212> TYPE: DNA
<213> ORGANISM: Artificial Sequence
<220> FEATURE:
<223> OTHER INFORMATION: target sequence

```
<400> SEQUENCE: 54
aagggctgga gctgtttgag a                                              21

<210> SEQ ID NO 55
<211> LENGTH: 21
<212> TYPE: DNA
<213> ORGANISM: Artificial Sequence
<220> FEATURE:
<223> OTHER INFORMATION: target sequence

<400> SEQUENCE: 55
aacacctcgg cccctacca g                                               21

<210> SEQ ID NO 56
<211> LENGTH: 21
<212> TYPE: DNA
<213> ORGANISM: Artificial Sequence
<220> FEATURE:
<223> OTHER INFORMATION: target sequence

<400> SEQUENCE: 56
aacttgtcag cccccgggtc c                                              21

<210> SEQ ID NO 57
<211> LENGTH: 21
<212> TYPE: DNA
<213> ORGANISM: Artificial Sequence
<220> FEATURE:
<223> OTHER INFORMATION: target sequence

<400> SEQUENCE: 57
aaccccacag tcacctatgg c                                              21

<210> SEQ ID NO 58
<211> LENGTH: 21
<212> TYPE: DNA
<213> ORGANISM: Artificial Sequence
<220> FEATURE:
<223> OTHER INFORMATION: target sequence

<400> SEQUENCE: 58
aacgactcct tctcggccaa g                                              21

<210> SEQ ID NO 59
<211> LENGTH: 21
<212> TYPE: DNA
<213> ORGANISM: Artificial Sequence
<220> FEATURE:
<223> OTHER INFORMATION: target sequence

<400> SEQUENCE: 59
aaggcctcag tcagtgtgac c                                              21

<210> SEQ ID NO 60
<211> LENGTH: 21
<212> TYPE: DNA
<213> ORGANISM: Artificial Sequence
<220> FEATURE:
<223> OTHER INFORMATION: target sequence

<400> SEQUENCE: 60
aatactgggg aaccagagcc a                                              21

<210> SEQ ID NO 61
<211> LENGTH: 21
<212> TYPE: DNA
```

```
<213> ORGANISM: Artificial Sequence
<220> FEATURE:
<223> OTHER INFORMATION: target sequence

<400> SEQUENCE: 61
aaccagagcc aggagacact g                                              21

<210> SEQ ID NO 62
<211> LENGTH: 21
<212> TYPE: DNA
<213> ORGANISM: Artificial Sequence
<220> FEATURE:
<223> OTHER INFORMATION: target sequence

<400> SEQUENCE: 62
aacgtgattc tgacgaagcc a                                              21

<210> SEQ ID NO 63
<211> LENGTH: 21
<212> TYPE: DNA
<213> ORGANISM: Artificial Sequence
<220> FEATURE:
<223> OTHER INFORMATION: target sequence

<400> SEQUENCE: 63
aagccagagg tctcagaagg g                                              21

<210> SEQ ID NO 64
<211> LENGTH: 21
<212> TYPE: DNA
<213> ORGANISM: Artificial Sequence
<220> FEATURE:
<223> OTHER INFORMATION: target sequence

<400> SEQUENCE: 64
aagggaccga ggtgacagtg a                                              21

<210> SEQ ID NO 65
<211> LENGTH: 21
<212> TYPE: DNA
<213> ORGANISM: Artificial Sequence
<220> FEATURE:
<223> OTHER INFORMATION: target sequence

<400> SEQUENCE: 65
aagtgtgagg cccaccctag a                                              21

<210> SEQ ID NO 66
<211> LENGTH: 21
<212> TYPE: DNA
<213> ORGANISM: Artificial Sequence
<220> FEATURE:
<223> OTHER INFORMATION: target sequence

<400> SEQUENCE: 66
aaggtgacgc tgaatggggt t                                              21

<210> SEQ ID NO 67
<211> LENGTH: 21
<212> TYPE: DNA
<213> ORGANISM: Artificial Sequence
<220> FEATURE:
<223> OTHER INFORMATION: target sequence

<400> SEQUENCE: 67
aatggggttc cagcccagcc a                                              21
```

<210> SEQ ID NO 68
<211> LENGTH: 21
<212> TYPE: DNA
<213> ORGANISM: Artificial Sequence
<220> FEATURE:
<223> OTHER INFORMATION: target sequence

<400> SEQUENCE: 68
aaggccaccc cagaggacaa c                                          21

<210> SEQ ID NO 69
<211> LENGTH: 21
<212> TYPE: DNA
<213> ORGANISM: Artificial Sequence
<220> FEATURE:
<223> OTHER INFORMATION: target sequence

<400> SEQUENCE: 69
aacgggcgca gcttctcctg c                                          21

<210> SEQ ID NO 70
<211> LENGTH: 21
<212> TYPE: DNA
<213> ORGANISM: Artificial Sequence
<220> FEATURE:
<223> OTHER INFORMATION: target sequence

<400> SEQUENCE: 70
aaccctggag gtggccggcc a                                          21

<210> SEQ ID NO 71
<211> LENGTH: 21
<212> TYPE: DNA
<213> ORGANISM: Artificial Sequence
<220> FEATURE:
<223> OTHER INFORMATION: target sequence

<400> SEQUENCE: 71
aagaaccaga cccgggagct t                                          21

<210> SEQ ID NO 72
<211> LENGTH: 21
<212> TYPE: DNA
<213> ORGANISM: Artificial Sequence
<220> FEATURE:
<223> OTHER INFORMATION: target sequence

<400> SEQUENCE: 72
aaccagaccc gggagcttcg t                                          21

<210> SEQ ID NO 73
<211> LENGTH: 21
<212> TYPE: DNA
<213> ORGANISM: Artificial Sequence
<220> FEATURE:
<223> OTHER INFORMATION: target sequence

<400> SEQUENCE: 73
aaactggacg tggccagaaa a                                          21

<210> SEQ ID NO 74
<211> LENGTH: 21
<212> TYPE: DNA
<213> ORGANISM: Artificial Sequence
<220> FEATURE:
<223> OTHER INFORMATION: target sequence

```
<400> SEQUENCE: 74
aactggacgt ggccagaaaa t                                              21

<210> SEQ ID NO 75
<211> LENGTH: 21
<212> TYPE: DNA
<213> ORGANISM: Artificial Sequence
<220> FEATURE:
<223> OTHER INFORMATION: target sequence

<400> SEQUENCE: 75
aaaattccca gcagactcca a                                              21

<210> SEQ ID NO 76
<211> LENGTH: 21
<212> TYPE: DNA
<213> ORGANISM: Artificial Sequence
<220> FEATURE:
<223> OTHER INFORMATION: target sequence

<400> SEQUENCE: 76
aaattcccag cagactccaa t                                              21

<210> SEQ ID NO 77
<211> LENGTH: 21
<212> TYPE: DNA
<213> ORGANISM: Artificial Sequence
<220> FEATURE:
<223> OTHER INFORMATION: target sequence

<400> SEQUENCE: 77
aattcccagc agactccaat g                                              21

<210> SEQ ID NO 78
<211> LENGTH: 21
<212> TYPE: DNA
<213> ORGANISM: Artificial Sequence
<220> FEATURE:
<223> OTHER INFORMATION: target sequence

<400> SEQUENCE: 78
aatgtgccag gcttggggga a                                              21

<210> SEQ ID NO 79
<211> LENGTH: 21
<212> TYPE: DNA
<213> ORGANISM: Artificial Sequence
<220> FEATURE:
<223> OTHER INFORMATION: target sequence

<400> SEQUENCE: 79
aacccattgc ccgagctcaa g                                              21

<210> SEQ ID NO 80
<211> LENGTH: 21
<212> TYPE: DNA
<213> ORGANISM: Artificial Sequence
<220> FEATURE:
<223> OTHER INFORMATION: target sequence

<400> SEQUENCE: 80
aagtgtctaa aggatggcac t                                              21

<210> SEQ ID NO 81
<211> LENGTH: 21
<212> TYPE: DNA
```

```
<213> ORGANISM: Artificial Sequence
<220> FEATURE:
<223> OTHER INFORMATION: target sequence

<400> SEQUENCE: 81
aaaggatggc actttcccac t                                               21

<210> SEQ ID NO 82
<211> LENGTH: 21
<212> TYPE: DNA
<213> ORGANISM: Artificial Sequence
<220> FEATURE:
<223> OTHER INFORMATION: target sequence

<400> SEQUENCE: 82
aaggatggca ctttcccact g                                               21

<210> SEQ ID NO 83
<211> LENGTH: 21
<212> TYPE: DNA
<213> ORGANISM: Artificial Sequence
<220> FEATURE:
<223> OTHER INFORMATION: target sequence

<400> SEQUENCE: 83
aatcagtgac tgtcactcga g                                               21

<210> SEQ ID NO 84
<211> LENGTH: 21
<212> TYPE: DNA
<213> ORGANISM: Artificial Sequence
<220> FEATURE:
<223> OTHER INFORMATION: target sequence

<400> SEQUENCE: 84
aaggggaggt cacccgcgag g                                               21

<210> SEQ ID NO 85
<211> LENGTH: 21
<212> TYPE: DNA
<213> ORGANISM: Artificial Sequence
<220> FEATURE:
<223> OTHER INFORMATION: target sequence

<400> SEQUENCE: 85
aatgtgctct ccccccggta t                                               21

<210> SEQ ID NO 86
<211> LENGTH: 21
<212> TYPE: DNA
<213> ORGANISM: Artificial Sequence
<220> FEATURE:
<223> OTHER INFORMATION: target sequence

<400> SEQUENCE: 86
aatgggcact gcaggcctca g                                               21

<210> SEQ ID NO 87
<211> LENGTH: 21
<212> TYPE: DNA
<213> ORGANISM: Artificial Sequence
<220> FEATURE:
<223> OTHER INFORMATION: target sequence

<400> SEQUENCE: 87
aaccgccagc ggaagatcaa g                                               21
```

```
<210> SEQ ID NO 88
<211> LENGTH: 21
<212> TYPE: DNA
<213> ORGANISM: Artificial Sequence
<220> FEATURE:
<223> OTHER INFORMATION: target sequence

<400> SEQUENCE: 88
aagatcaaga aatacagact a                                             21

<210> SEQ ID NO 89
<211> LENGTH: 21
<212> TYPE: DNA
<213> ORGANISM: Artificial Sequence
<220> FEATURE:
<223> OTHER INFORMATION: target sequence

<400> SEQUENCE: 89
aagaaataca gactacaaca g                                             21

<210> SEQ ID NO 90
<211> LENGTH: 21
<212> TYPE: DNA
<213> ORGANISM: Artificial Sequence
<220> FEATURE:
<223> OTHER INFORMATION: target sequence

<400> SEQUENCE: 90
aaatacagac tacaacaggc c                                             21

<210> SEQ ID NO 91
<211> LENGTH: 21
<212> TYPE: DNA
<213> ORGANISM: Artificial Sequence
<220> FEATURE:
<223> OTHER INFORMATION: target sequence

<400> SEQUENCE: 91
aatacagact acaacaggcc c                                             21

<210> SEQ ID NO 92
<211> LENGTH: 21
<212> TYPE: DNA
<213> ORGANISM: Artificial Sequence
<220> FEATURE:
<223> OTHER INFORMATION: target sequence

<400> SEQUENCE: 92
aacaggccca aaaagggacc c                                             21

<210> SEQ ID NO 93
<211> LENGTH: 21
<212> TYPE: DNA
<213> ORGANISM: Artificial Sequence
<220> FEATURE:
<223> OTHER INFORMATION: target sequence

<400> SEQUENCE: 93
aaaaagggac ccccatgaaa c                                             21

<210> SEQ ID NO 94
<211> LENGTH: 21
<212> TYPE: DNA
<213> ORGANISM: Artificial Sequence
```

-continued

```
<220> FEATURE:
<223> OTHER INFORMATION: target sequence

<400> SEQUENCE: 94
aaaagggacc cccatgaaac c                                              21
```

COMPOSITIONS AND METHODS FOR SIRNA INHIBITION OF ICAM-1

CROSS REFERENCE TO RELATED APPLICATIONS

This application is a continuation of U.S. nonprovisional patent application Ser. No. 12/329,221, filed on Dec. 5, 2008 entitled "COMPOSITIONS AND METHODS FOR SIRNA INHIBITION OF ICAM-1", which is a continuation of U.S. nonprovisional patent application Ser. No. 10/759,878, filed on Jan. 16, 2004, now abandoned, and claims the benefit of U.S. provisional patent application Ser. No. 60/440,579, filed on Jan. 16, 2003; the contents of which are herein incorporated by reference in their entirety.

FIELD OF THE INVENTION

This invention relates to the regulation of ICAM-1 gene expression by small interfering RNA, in particular for treating diseases or conditions involving intercellular adhesion.

BACKGROUND OF THE INVENTION

Many physiological processes require that cells come into close contact with and adhere to other cells or the extracellular matrix. Cell-cell and cell-matrix interactions are mediated through several families of intercellular adhesion molecules or "ICAMs."

ICAM-1 is a 110 kilodalton member of the immunoglobulin superfamily (Simmons et al., 1988, Nature (London) 331: 624-627) that is expressed on a limited number of cells and at low levels in the absence of stimulation (Dustin et al., 1986 J. Immunol. 137, 245-254). Upon stimulation with inflammatory mediators, a variety of cell types in different tissues express high levels of ICAM-1 on their surface (Springer et. al. supra; Dustin et al., supra; and Rothlein et al., 1988, J. Immunol. 141: 1665-1669). Cells which can express ICAM-1 upon stimulation include non-hematopoietic cells such as vascular endothelial cells, thymic and other epithelial cells, and fibroblasts; and hematopoietic cells such as tissue macrophages, mitogen-stimulated T lymphocyte blasts, and germinal center dendritic cells in tonsils, lymph nodes, and Peyer's patches. ICAM-1 induction occurs via increased transcription of ICAM-1 mRNA (Simmons et al., supra), which is detectable at 4 hours post-induction and peaks at 16-24 hours post-induction.

In vitro studies have shown that antibodies to ICAM-1 block adhesion of leukocytes to cytokine-activated endothelial cells (Boyd et al., 1988, Proc. Natl. Acad. Sci. USA 85: 3095-3099; Dustin and Springer, 1988, J. Cell Biol. 107: 321-331). Thus, ICAM-1 expression appears to be required for the extravasation of immune cells to sites of inflammation. Antibodies to ICAM-1 also block T cell killing, mixed lymphocyte reactions, and T cell-mediated B cell differentiation, indicating that ICAM-1 is required for these cognate cell interactions (Boyd et al., supra). The involvement of ICAM-1 in antigen presentation is shown by the inability of ICAM-1 defective murine B cell mutants to stimulate antigen-dependent T cell proliferation (Dang et al., 1990, J. Immunol. 144: 4082-4091). Conversely, murine L cells require transfection with human ICAM-1 in addition to HLA-DR in order to present antigen to human T cells (Altmann et al., 1989, Nature (London) 338: 512-514). Thus, blocking ICAM-1 function can prevent immune cell recognition and activity during transplant rejection, and can be effective in treating animal models of rheumatoid arthritis, asthma and reperfusion injury.

Expression of ICAM-1 has also been associated with a variety of inflammatory skin disorders such as allergic contact dermatitis, fixed drug eruption, lichen planus, and psoriasis (Ho et al., 1990, J. Am. Acad. Dermatol., 22: 64-68; Griffiths and Nickoloff, 1989, Am. J. Pathology 135: 1045-1053; Lisby et al., 1989, Br. J. Dermatol. 120: 479-484; Shiohara et al., 1989, Arch. Dermatol. 125: 1371-1376). In addition, ICAM-1 expression has been detected in the synovium of patients with rheumatoid arthritis (Hale et al., 1989, Arth. Rheum., 32: 22-30), in the pancreatic B-cells of diabetics (Campbell et al., 1989, P.N.A.S. USA 86: 4282-4286); in thyroid follicular cells of patients with Graves' disease (Weetman et al., 1989, J. Endocrinol. 122: 185-191); in renal and liver allograft rejection (Fault and Russ, 1989, Transplantation 48: 226-230; Adams et al., 1989, Lancet 1122-1125); and in inflammatory bowel disease (IBD) tissue (Springer T, 1990, Nature 346: 425-34).

ICAM-1 expression is also implicated in angiogenesis, which is the formation of new blood vessels from the endothelial cells of preexisting blood vessels. Angiogenesis is a complex process which involves a changing profile of endothelial cell gene expression associated with cell migration, proliferation, and differentiation, which begins with localized breakdown of the basement membrane of the parent vessel. The endothelial cells then migrate away from the parent vessel into the interstitial extracellular matrix (ECM) to form a capillary sprout, which elongates due to continued migration and proliferation of endothelial cells in the ECM. The interactions of the endothelial cells with the ECM during angiogenesis require alterations of cell-matrix contacts which are caused, in part, by an increase in ICAM-1 expression.

Aberrant angiogenesis, or the pathogenic growth of new blood vessels, is implicated in a number of conditions. Among these conditions are diabetic retinopathy, psoriasis, exudative or "wet" age-related macular degeneration ("AMD"), rheumatoid arthritis and other inflammatory diseases, and most cancers. AMD in particular is a clinically important angiogenic disease. This condition is characterized by choroidal neovascularization in one or both eyes in aging individuals, and is the major cause of blindness in industrialized countries.

Several complications commonly seen in type I diabetes also involve expression of ICAM-1. For example, ICAM-1-mediated adhesion of leukocytes to capillary endothelium (also called "leukostasis") can cause microvascular ischemia in certain tissues of diabetics, such as the retina, peripheral nerves, and kidney. This results in capillary non-perfusion of these tissues, which in turn leads to diabetic retinopathy (Miyamoto K et al. (2000), Am. J. Pathol. 156: 1733-1739; Miyamoto K et al. (1999), P.N.A.S USA 96:10836-1084), neuropathy (Jude E B et al. (1998), Diabetologia 41:330-6) or nephropathy. Miyamoto et al. (1999, P.N.A.S USA 96: 10836-10841) suggest that inhibition of ICAM-1-mediated leukostasis can prevent retinal abnormalities associated with diabetes. However, at least one study reported that the development of diabetic nephropathy in the "Wistar fatty" rat model of diabetes does not appear to involve ICAM-1 expression in glomeruli (Matsui H et al. (1996), Diabetes Res. Clin. Pract. 32:1-9).

ICAM-1 has also been implicated in the onset of macrovascular disease (e.g., coronary artery disease, cerebrovascular disease, and peripheral vascular disease) in type I diabetes, which results in part from accelerated atherosclerosis and increased thrombosis. For example, ICAM-1 has been found in atherosclerotic plaques and is likely involved in the initiation and development of atherosclerosis in diabetics. (Jude E B et al. (2002), *Eur. J. Intern. Med.* 13:185-189).

ICAM-1 therefore plays an essential role in both normal and pathophysiological processes (Springer et al., 1987, *Ann. Rev. Immunol.* 5: 223-252). Strategies have therefore been developed to mediate cell adhesion by blocking ICAM-1 function or expression. Such strategies typically employ anti-ICAM-1 antibodies, ligands which competitively block ICAM-1 binding, or antisense nucleic acid molecules directed against ICAM-1 mRNA. However, the agents used in such therapies produce only a stoichiometric reduction in ICAM-1, and are typically overwhelmed by the abnormally high production of ICAM-1 by the diseased or activated cells. The results achieved with these strategies have therefore been unsatisfactory.

RNA interference (hereinafter "RNAi") is a method of post-transcriptional gene regulation that is conserved throughout many eukaryotic organisms. RNAi is induced by short (i.e., <30 nucleotide) double stranded RNA ("dsRNA") molecules which are present in the cell (Fire A et al. (1998), *Nature* 391: 806-811). These short dsRNA molecules, called "short interfering RNA" or "siRNA," cause the destruction of messenger RNAs ("mRNAs") which share sequence homology with the siRNA to within one nucleotide resolution (Elbashir S M et al. (2001), *Genes Dev,* 15: 188-200). It is believed that the siRNA and the targeted mRNA bind to an "RNA-induced silencing complex" or "RISC", which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

Elbashir S M et al. (2001), supra, have shown that synthetic siRNA of 21 and 22 nucleotides in length, and which have short 3' overhangs, are able to induce RNAi of target mRNA in a Drosophila cell lysate. Cultured mammalian cells also exhibit RNAi degradation with synthetic siRNA (Elbashir S M et al. (2001) *Nature,* 411: 494-498), and RNAi degradation induced by synthetic siRNA has recently been shown in living mice (McCaffrey A P et al. (2002), *Nature,* 418: 38-39; Xia H et al. (2002), *Nat. Biotech.* 20: 1006-1010). The therapeutic potential of siRNA-induced RNAi degradation has been demonstrated in several recent in vitro studies, including the siRNA-directed inhibition of HIV-1 infection (Novina C D et al. (2002), *Nat. Med.* 8: 681-686) and reduction of neurotoxic polyglutamine disease protein expression (Xia H et al. (2002), supra).

What is needed, therefore, are agents in catalytic or sub-stoichiometric amounts which selectively inhibit expression of ICAM-1, in order to effectively decrease or block ICAM-1-mediated cell adhesion.

SUMMARY OF THE INVENTION

The present invention is directed to siRNA which specifically target and cause RNAi-induced degradation of mRNA from ICAM-1 genes. The siRNA compounds and compositions of the invention are used to treat cell adhesion and cell adhesion-mediated pathologies. In particular, the siRNA of the invention are useful for inhibiting angiogenesis, for example in the treatment of cancerous tumors, age-related macular degeneration, and other angiogenic diseases.

Thus, the invention provides an isolated siRNA which targets human ICAM-1 mRNA, or an alternative splice form, mutant or cognate thereof. The siRNA comprises a sense RNA strand and an antisense RNA strand which form an RNA duplex. The sense RNA strand comprises a nucleotide sequence substantially identical to a target sequence of about 19 to about 25 contiguous nucleotides in the target mRNA.

The invention also provides recombinant plasmids and viral vectors which express the siRNA of the invention, as well as pharmaceutical compositions comprising the siRNA of the invention and a pharmaceutically acceptable carrier.

The invention further provides a method of inhibiting expression of human ICAM-1 mRNA, or an alternative splice form, mutant or cognate thereof, comprising administering to a subject an effective amount of the siRNA of the invention such that the target mRNA is degraded.

The invention further provides a method of treating cell adhesion or cell adhesion-mediated pathologies, comprising administering to a subject in need of such treatment an effective amount of an siRNA targeted to human ICAM-1 mRNA, or an alternative splice form, mutant or cognate thereof.

The invention further provides a method of inhibiting angiogenesis in a subject, comprising administering to a subject an effective amount of an siRNA targeted to human ICAM-1 mRNA, or an alternative splice form, mutant or cognate thereof.

The invention still further provides a method of treating complications arising from type I diabetes in a subject, comprising administering to a subject in need of such treatment an effective amount of an siRNA targeted to human ICAM-1 mRNA, or an alternative splice form, mutant or cognate thereof.

DETAILED DESCRIPTION OF THE INVENTION

Figure 1:
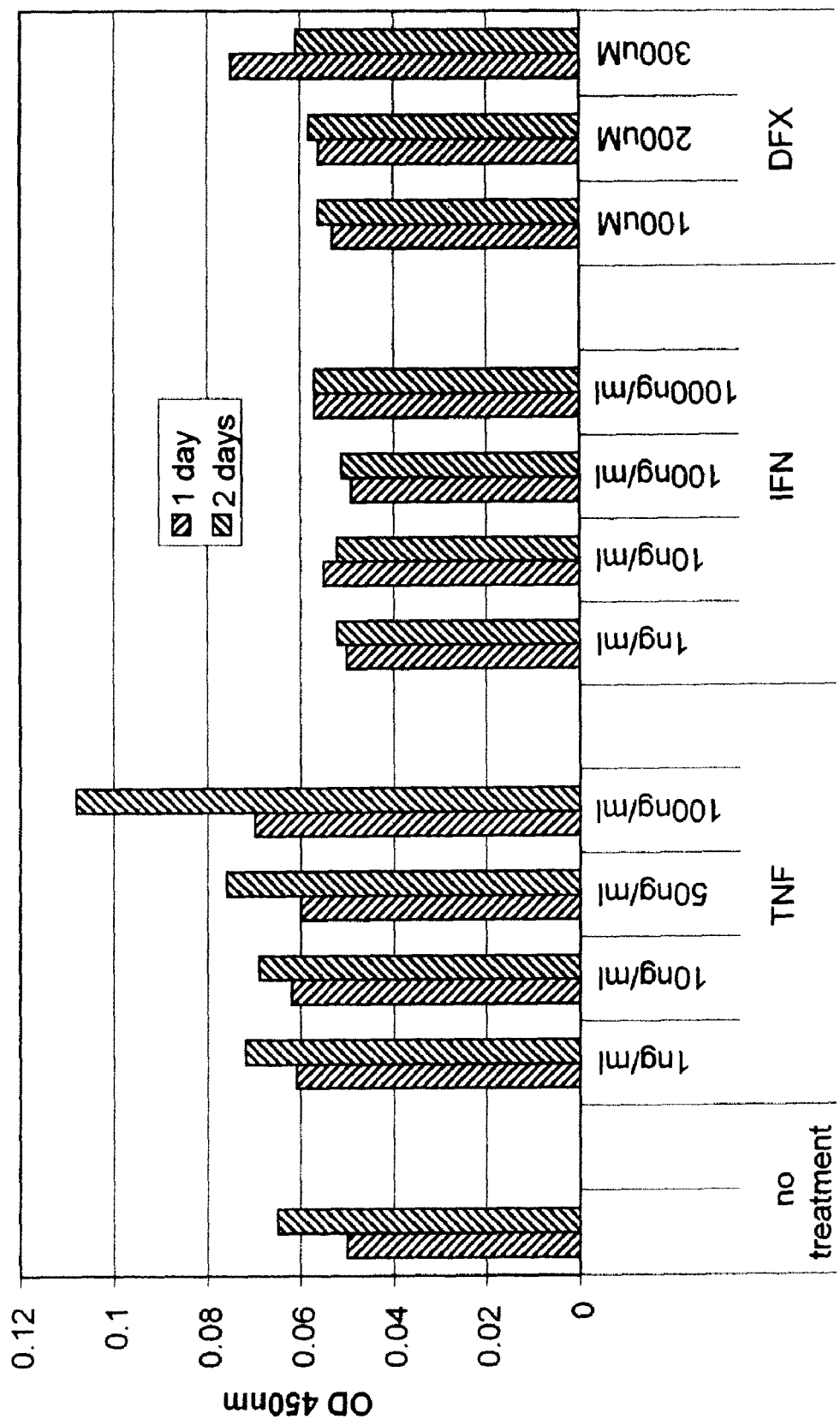
FIG. 1 is a histogram of human ICAM-1 protein concentration, as measured by ELISA at $OD_{450}$ nanometers, in lysates of untreated HEK-293 cells ("no treatment"), or of HEK-293 cells treated with tumor necrosis factor alpha ("TNF-α") at 1, 10, 50, and 100 ng/ml; interferon gamma ("IFN-γ") at 1, 10, 100, 1000 ng/ml; or desferrioxamine ("DFX") at 100, 200, and 300 uM for one or two days.

Unless otherwise indicated, all nucleic acid sequences herein are given in the 5' to 3' direction. Also, all deoxyribonucleotides in a nucleic acid sequence are represented by capital letters (e.g., deoxythymidine is "T"), and ribonucleotides in a nucleic acid sequence are represented by lower case letters (e.g., uridine is "u").

Compositions and methods comprising siRNA targeted to ICAM-1 mRNA are advantageously used in the inhibition or prevention of cell adhesion and cell-adhesion mediated pathologies. As used herein, "cell adhesion and cell-adhesion mediated pathologies" refer to any disease or condition in which ICAM-1-mediated adhesion of one cell to another, or to the extracellular matrix, is required for initiation and/or maintenance of the disease or condition. One skilled in the art is familiar with such diseases and conditions; for example, angiogenesis requires the ICAM-1-mediated adhesion of endothelial cells to the extracellular matrix. Also, the extravasation of immune cells to sites of inflammation requires ICAM-1-mediated adhesion of leukocytes to cytokine-activated endothelial cells. Other cell adhesion and cell-adhesion mediated pathologies include AIDS-related dementia, allergic conjunctivitis, allergic rhinitis, Alzheimer's disease, angiogenesis (including both pathologic and non-pathologic angiogenesis), antigen presentation, asthma, atherosclerosis, certain types of toxic and immune-based nephritis, contact dermal hypersensitivity, corneal/limbic injury, type I diabetes and complications arising from type I diabetes, such as diabetic retinopathy, diabetic neuropathy, diabetic nephropathy, and macrovascular disease, Graves' disease, inflammatory bowel disease (including ulcerative colitis and Crohn's disease), inflammatory lung diseases, inflammatory sequelae of viral infections, inflammatory skin disorders (e.g., allergic contact dermatitis, fixed drug eruption, lichen planus, and psoriasis), immune cell recognition and activity during transplant (allograft) rejection, including rejection of renal, liver and bone marrow transplants, immune cell interactions (such as T-cell killing, mixed lymphocyte reactions, and T-cell mediated B-cell differentiation), meningitis, multiple sclerosis, multiple myeloma, myocarditis, pulmonary fibrosis, reperfusion injury, restenosis, retinitis, rheumatoid arthritis, septic arthritis, stroke, tumor growth and metastasis, and uveitis.

The siRNA of the invention cause the RNAi-mediated degradation of ICAM-1 mRNA, so that the protein product of the ICAM-1 gene is not produced or is produced in reduced amounts. Because the ICAM-1 gene product is required for certain intercellular or cell-ECM adhesion events, the siRNA-mediated degradation of ICAM-1 mRNA inhibits intercellular or cell-ECM adhesion. Cell adhesion or cell-mediated adhesion pathologies can thus be treated by inducing RNAi degradation of ICAM-1 mRNA with the siRNA of the invention.

The invention therefore provides isolated siRNA comprising short double-stranded RNA from about 17 nucleotides to about 29 nucleotides in length, preferably from about 19 to about 25 nucleotides in length, that are targeted to the target mRNA. The siRNA comprise a sense RNA strand and a complementary antisense RNA strand annealed together by standard Watson-Crick base-pairing interactions (hereinafter "base-paired"). As is described in more detail below, the sense strand comprises a nucleic acid sequence which is substantially identical to a target sequence contained within the target mRNA.

As used herein, a nucleic acid sequence "substantially identical" to a target sequence contained within the target mRNA is a nucleic acid sequence which is identical to the target sequence, or which differs from the target sequence by one or more nucleotides. Sense strands of the invention which comprise nucleic acid sequences substantially identical to a target sequence are characterized in that siRNA comprising such sense strands induce RNAi-mediated degradation of mRNA containing the target sequence. For example, an siRNA of the invention can comprise a sense strand comprise nucleic acid sequences which differ from a target sequence by one, two or three or more nucleotides, as long as RNAi-mediated degradation of the target mRNA is induced by the siRNA.

The sense and antisense strands of the present siRNA can comprise two complementary, single-stranded RNA molecules or can comprise a single molecule in which two complementary portions are base-paired and are covalently linked by a single-stranded "hairpin" area. Without wishing to be bound by any theory, it is believed that the hairpin area of the latter type of siRNA molecule is cleaved intracellularly by the "Dicer" protein (or its equivalent) to form a siRNA of two individual base-paired RNA molecules (see Tuschl, T. (2002), supra).

As used herein, "isolated" means synthetic, or altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered. By way of example, siRNA which are produced inside a cell by natural processes, but which are produced from an "isolated" precursor molecule, are "isolated" molecules. Thus, an isolated dsRNA or protein can be introduced into a target cell, where it is processed by the Dicer protein (or its equivalent) into isolated siRNA.

As used herein, "target mRNA" means human ICAM-1 mRNA, mutant or alternative splice forms of human ICAM-1 mRNA, or mRNA from cognate ICAM-1 genes. The human ICAM-1 mRNA sequence is given in SEQ ID NO: 1 as the cDNA equivalent. One skilled in the art would understand that the cDNA sequence is equivalent to the mRNA sequence, and can be used for the same purpose herein; i.e., the generation of siRNA for inhibiting expression of ICAM-1.

As used herein, a gene or mRNA which is "cognate" to human ICAM-1 is a gene or mRNA from another mammalian species which is homologous to human ICAM-1. For example, the cognate ICAM-1 mRNA from the mouse is given in SEQ ID NO: 2 as the cDNA equivalent.

The mRNA transcribed from the human ICAM-1 gene can be analyzed for alternative splice forms using techniques well-known in the art. Such techniques include reverse transcription-polymerase chain reaction (RT-PCR), northern blotting and in-situ hybridization. Techniques for analyzing mRNA sequences are described, for example, in Busting S A (2000), *J. Mol. Endocrinol.* 25: 169-193, the entire disclosure of which is herein incorporated by reference. Representative techniques for identifying alternatively spliced mRNAs are also described below.

For example, databases that contain nucleotide sequences related to a given disease gene can be used to identify alternatively spliced mRNA. Such databases include GenBank, Embase, and the Cancer Genome Anatomy Project (CGAP) database. The CGAP database, for example, contains expressed sequence tags (ESTs) from various types of human cancers. An mRNA or gene sequence from the ICAM-1 gene can be used to query such a database to determine whether ESTs representing alternatively spliced mRNAs have been found.

A technique called "RNAse protection" can also be used to identify alternatively spliced ICAM-1 mRNAs. RNAse protection involves translation of a gene sequence into synthetic RNA, which is hybridized to RNA derived from other cells; for example, cells which are induced to express ICAM-1. The hybridized RNA is then incubated with enzymes that recognize RNA:RNA hybrid mismatches. Smaller than expected fragments indicate the presence of alternatively spliced mRNAs. The putative alternatively spliced mRNAs can be cloned and sequenced by methods well known to those skilled in the art.

RT-PCR can also be used to identify alternatively spliced ICAM-1 mRNAs. In RT-PCR, mRNA from activated leukocytes, cells from inflammatory bowel disease tissue, or cells from other tissue known to express ICAM-1 is converted into cDNA by the enzyme reverse transcriptase, using methods well-known to those of ordinary skill in the art. The entire coding sequence of the cDNA is then amplified via PCR using a forward primer located in the 3' untranslated region, and a reverse primer located in the 5' untranslated region. The amplified products can be analyzed for alternative splice forms, for example by comparing the size of the amplified products with the size of the expected product from normally spliced mRNA, e.g., by agarose gel electrophoresis. Any change in the size of the amplified product can indicate alternative splicing.

The mRNA produced from mutant ICAM-1 genes can also be readily identified with the techniques described above for identifying ICAM-1 alternative splice forms. As used herein, "mutant" ICAM-1 genes or mRNA include human ICAM-1 genes or mRNA which differ in sequence from the ICAM-1 sequences set forth herein. Thus, allelic forms of the ICAM-1 gene, and the mRNA produced from them, are considered "mutants" for purposes of this invention.

It is understood that human ICAM-1 mRNA may contain target sequences in common with its respective alternative splice forms, cognates or mutants. A single siRNA comprising such a common targeting sequence can therefore induce RNAi-mediated degradation of those different mRNAs which contain the common targeting sequence.

The siRNA of the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA; modifications that make the siRNA resistant to nuclease digestion (e.g., the use of 2'-substituted ribonucleotides or modifications to the sugar-phosphate backbone); or the substitution of one or more nucleotides in the siRNA with deoxyribonucleotides. siRNA which are exposed to serum, lachrymal fluid or other nuclease-rich environments, or which are delivered topically (e.g., by eyedropper), are preferably altered to increase their resistance to nuclease degradation. For example, siRNA which are administered intravascularly or topically to the eye can comprise one or more phosphorothioate linkages.

One or both strands of the siRNA of the invention can also comprise a 3' overhang. As used herein, a "3' overhang" refers to at least one unpaired nucleotide extending from the 3'-end of an RNA strand.

Thus in one embodiment, the siRNA of the invention comprises at least one 3' overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length.

In the embodiment in which both strands of the siRNA molecule comprise a 3' overhang, the length of the overhangs can be the same or different for each strand. In a most preferred embodiment, the 3' overhang is present on both strands of the siRNA, and is 2 nucleotides in length. For example, each strand of the siRNA of the invention can comprise 3' overhangs of dithymidylic acid ("TT") or diuridylic acid ("uu").

In order to enhance the stability of the present siRNA, the 3' overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2' hydroxyl in the 2'-deoxythymidine significantly enhances the nuclease resistance of the 3' overhang in tissue culture medium.

In certain embodiments, the siRNA of the invention comprises the sequence AA(N19)TT or NA(N21), where N is any nucleotide. These siRNA comprise approximately 30-70% GC, and preferably comprise approximately 50% G/C. The sequence of the sense siRNA strand corresponds to (N19)TT or N21 (i.e., positions 3 to 23), respectively. In the latter case, the 3' end of the sense siRNA is converted to TT. The rationale for this sequence conversion is to generate a symmetric duplex with respect to the sequence composition of the sense and antisense strand 3' overhangs. The antisense RNA strand is then synthesized as the complement to positions 1 to 21 of the sense strand.

Because position 1 of the 23-nt sense strand in these embodiments is not recognized in a sequence-specific manner by the antisense strand, the 3'-most nucleotide residue of the antisense strand can be chosen deliberately. However, the penultimate nucleotide of the antisense strand (complementary to position 2 of the 23-nt sense strand in either embodiment) is generally complementary to the targeted sequence.

In another embodiment, the siRNA of the invention comprises the sequence NAR(N17)YNN, where R is a purine (e.g., A or G) and Y is a pyrimidine (e.g., C or U/T). The respective 21-nt sense and antisense RNA strands of this embodiment therefore generally begin with a purine nucleotide. Such siRNA can be expressed from pol III expression vectors without a change in targeting site, as expression of RNAs from pol III promoters is only believed to be efficient when the first transcribed nucleotide is a purine.

The siRNA of the invention can be targeted to any stretch of approximately 19-25 contiguous nucleotides in any of the target mRNA sequences (the "target sequence"). Techniques for selecting target sequences for siRNA are given, for example, in Tuschl T et al., "The siRNA User Guide," revised Oct. 11, 2002, the entire disclosure of which is herein incorporated by reference. "The siRNA User Guide" is available on the world wide web at a website maintained by Dr. Thomas Tuschl, Department of Cellular Biochemistry, AG 105, Max-Planck-Institute for Biophysical Chemistry, 37077 Göttingen, Germany, and can be found by accessing the website of the Max Planck Institute and searching with the keyword "siRNA." Thus, the sense strand of the present siRNA comprises a nucleotide sequence substantially identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nt downstream (i.e., in the 3' direction) from the start codon. The target sequence can, however, be located in the 5' or 3' untranslated regions, or in the region nearby the start codon. For example, a suitable target sequence in the ICAM-1 cDNA sequence is:

```
GTTGTTGGGCATAGAGACC        (SEQ ID NO: 3)
```

Thus, an siRNA of the invention targeting this sequence, and which has 3' uu overhangs on each strand (overhangs shown in bold), is:

```
5'- guuguugggcauagagaccuu -3'    (SEQ ID NO: 4)

3'- uucaacaacccguaucucugg -5'    (SEQ ID NO: 5)
```

An siRNA of the invention targeting SEQ ID NO: 3, but having 3' TT overhangs on each strand (overhangs shown in bold) is:

```
5'- guuguugggcauagagaccTT -3'    (SEQ ID NO: 6)

3' -TTcaacaacccguaucucugg -5'    (SEQ ID NO: 7)
```

Other ICAM-1 target sequences from which siRNA of the invention can be derived include those given in Table 1, and those given as SEQ ID NOS 20-94. It is understood that the target sequences given herein are with reference to the human ICAM-1 cDNA, and thus these sequences contain deoxythymidines represented by "T." One skilled in the art would understand that, in the actual target sequence of the ICAM-1 mRNA, the deoxythymidines would be replaced by uridines ("u"). Likewise, a target sequence contained within an siRNA of the invention would also contain uridines in place of deoxythymidines.

TABLE 1

ICAM-1 Target Sequences

| target sequence | SEQ ID NO: |
|---|---|
| GGAGTTGCTCCTGCCTGGG | 8 |
| CCGGAAGGTGTATGAACTG | 9 |
| CTGAGCAATGTGCAAGAAG | 10 |
| TGTGCTATTCAAACTGCCC | 11 |
| CCTTCCTCACCGTGTACTG | 12 |
| CGGGTGGAACTGGCACCCC | 13 |
| CCTTACCCTACGCTGCCAG | 14 |
| CCTCACCGTGGTGCTGCTC | 15 |
| CGGGAGCCAGCTGTGGGGG | 16 |
| TTTCTCGTGCCGCACTGAA | 17 |
| CTGGACCTGCGGCCCCAAG | 18 |
| GGCCTCAGTCAGTGTGACC | 19 |

The siRNA of the invention can be obtained using a number of techniques known to those of skill in the art. For example, the siRNA can be chemically synthesized or recombinantly produced using methods known in the art, such as the Drosophila in vitro system described in U.S. published application 2002/0086356 of Tuschl et al., the entire disclosure of which is herein incorporated by reference.

Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, siRNA can also be expressed from recombinant circular or linear DNA plasmids using any suitable promoter. Suitable promoters for expressing siRNA of the invention from a plasmid include, for example, the U6 or H1 RNA pol III promoter sequences and the cytomegalovirus promoter. Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly. The use of recombinant plasmids to deliver siRNA of the invention to cells in vivo is discussed in more detail below.

siRNA of the invention can be expressed from a recombinant plasmid either as two separate, complementary RNA molecules, or as a single RNA molecule with two complementary regions.

Selection of plasmids suitable for expressing siRNA of the invention, methods for inserting nucleic acid sequences for expressing the siRNA into the plasmid, and methods of delivering the recombinant plasmid to the cells of interest are within the skill in the art. See, for example Tuschl, T. (2002), Nat. Biotechnol, 20: 446-448; Brummelkamp T R et al. (2002), Science 296: 550-553; Miyagishi M et al. (2002), Nat. Biotechnol. 20: 497-500; Paddison P J et al. (2002), Genes Dev. 16: 948-958; Lee N S et al. (2002), Nat. Biotechnol. 20: 500-505; and Paul C P et al. (2002), Nat. Biotechnol. 20: 505-508, the entire disclosures of which are herein incorporated by reference.

In one embodiment, a plasmid expressing an siRNA of the invention comprises a sense RNA strand coding sequence in operable connection with a polyT termination sequence under the control of a human U6 RNA promoter, and an antisense RNA strand coding sequence in operable connection with a polyT termination sequence under the control of a human U6 RNA promoter. Such a plasmid can be used in producing an recombinant adeno-associated viral vector for expressing an siRNA of the invention.

As used herein, "in operable connection with a polyT termination sequence" means that the nucleic acid sequences encoding the sense or antisense strands are immediately adjacent to the polyT termination signal in the 5' direction. During transcription of the sense or antisense sequences from the plasmid, the polyT termination signals act to terminate transcription.

As used herein, "under the control" of a promoter means that the nucleic acid sequences encoding the sense or antisense strands are located 3' of the promoter, so that the promoter can initiate transcription of the sense or antisense coding sequences.

The siRNA of the invention can also be expressed from recombinant viral vectors intracellularly in vivo. The recombinant viral vectors of the invention comprise sequences encoding the siRNA of the invention and any suitable promoter for expressing the siRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the siRNA in a particular tissue or in a particular intracellular environment. The use of recombinant viral vectors to deliver siRNA of the invention to cells in vivo is discussed in more detail below.

siRNA of the invention can be expressed from a recombinant viral vector either as two separate, complementary RNA molecules, or as a single RNA molecule with two complementary regions.

Any viral vector capable of accepting the coding sequences for the siRNA molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J E et al. (2002), *J Virol* 76:791-801, the entire disclosure of which is herein incorporated by reference.

Selection of recombinant viral vectors suitable for use in the invention, methods for inserting nucleic acid sequences for expressing the siRNA into the vector, and methods of delivering the viral vector to the cells of interest are within the skill in the art. See, for example, Dornburg R (1995), *Gene Therap.* 2: 301-310; Eglitis M A (1988), *Biotechniques* 6: 608-614; Miller A D (1990), *Hum Gene Therap.* 1: 5-14; and Anderson W F (1998), *Nature* 392: 25-30, the entire disclosures of which are herein incorporated by reference.

Preferred viral vectors are those derived from lentivirus, AV or AAV. In a particularly preferred embodiment, the siRNA of the invention is expressed as two separate, complementary single-stranded RNA molecules from a recombinant AAV vector comprising, for example, either the U6 or H1 RNA promoters, or the cytomegalovirus (CMV) promoter.

A suitable AV vector for expressing the siRNA of the invention, a method for constructing the recombinant AV vector, and a method for delivering the vector into target cells, are described in Xia H et al. (2002), *Nat. Biotech.* 20: 1006-1010.

Suitable AAV vectors for expressing the siRNA of the invention, methods for constructing the recombinant AV vector, and methods for delivering the vectors into target cells are described in Samulski R et al. (1987), *J. Virol.* 61: 3096-3101; Fisher K J et al. (1996), *J. Virol.,* 70: 520-532; Samulski R et al. (1989), *J. Virol.* 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

The ability of an siRNA containing a given target sequence to cause RNAi-mediated degradation of the target mRNA can be evaluated using standard techniques for measuring the levels of RNA or protein in cells. For example, siRNA of the invention can be delivered to cultured cells, and the levels of target mRNA can be measured by Northern blot or dot blotting techniques, or by quantitative RT-PCR. Alternatively, the levels of ICAM-1 protein in the cultured cells can be measured by ELISA or Western blot.

For example, cells which naturally express ICAM-1, or which are induced to express ICAM-1, are grown to confluence in 96 well microtiter plates. For cells which naturally express ICAM-1, the cells can be stimulated with either interleukin-1 or tumor necrosis factor for 8 to 24 hours to stimulate ICAM-1 expression. siRNA of the invention can be administered to one group of ICAM-1 expressing cells. A non-specific siRNA (or no siRNA) can be administered to a second group of ICAM-1 expressing cells as a control. The cells are washed and directly fixed to the microtiter plate wells with 1 to 2% paraformaldehyde. Nonspecific binding sites on the microtiter plate are blocked with 2% bovine serum albumin, and the cells incubated with an ICAM-1 specific monoclonal antibody. Bound ICAM-1 antibody can be detected, for example, by incubation with a 1:1000 dilution of biotinylated goat anti-mouse IgG (Bethesda Research Laboratories, Gaithersberg, Md.) for 1 hour at 37° C. and with a 1:1000 dilution of streptavidin conjugated to beta-galactosidase (Bethesda Research Laboratories) for 1 hour at 37° C. The amount of beta-galactosidase bound to the ICAM-1 specific monoclonal antibody is determined, for example, by developing the microtiter plate in a solution of 3.3 mM chlorophenolred-beta-D-galactopyranoside, 50 mM sodium phosphate, 1.5 mM $MgCl_2$; pH 7.2 for 2 to 15 minutes at 37° C., and measuring the concentration of bound antibody at 575 nm in an ELISA microtiter plate reader.

The ability of the present siRNA to down-regulate ICAM-1 expression can also be evaluated in vitro by measuring neurite outgrowth, adhesion between endothelial cells, adhesion between epithelial cells (e.g., normal rat kidney cells and/or human skin), or adhesion between cancer cells by techniques which are within the skill in the art.

A suitable neurite outgrowth assay comprises culturing neurons on a monolayer of cells that express ICAM-1 naturally or which are induced to express ICAM-1. Neurons grown on ICAM-1 expressing cells extend longer neurites than neurons cultured on cells that do not express ICAM-1. For example, neurons can be cultured on monolayers of 3T3 cells transfected with cDNA encoding ICAM-1 essentially as described by Doherty and Walsh, 1994, *Curr. Op. Neurobiol.* 4: 49-55 and Safell et al., 1997, *Neuron* 18: 231-242, the entire disclosures of which are herein incorporated by reference. Briefly, monolayers of control 3T3 fibroblasts and 3T3 fibroblasts that express ICAM-1 can be established by overnight culture of 80,000 cells in individual wells of an 8-well tissue culture dish. Three thousand cerebellar neurons isolated from post-natal day 3 mouse brains can be cultured for 18 hours on the various monolayers. The cultures can then be fixed and stained with neuron-specific antibodies (e.g., GAP43) using standard techniques. The neurite lengths of control cells and cells treated with the siRNA of the invention can be measured by computer assisted morphometry. siRNA-induced RNAi degradation of ICAM-1 mRNA in test cells is indicated by an increase in mean neurite length by at least 50% as compared to the control cells.

RNAi degradation of ICAM-1 by the present siRNA can also be evaluated by detecting the disruption of cell adhesion. For example, cells which express ICAM-1 naturally or which are induced to express ICAM-1 can be plated under standard conditions that permit cell adhesion. Disruption of cell adhesion upon administration of an siRNA of the invention can be determined visually within 24 hours, by observing retraction of the cells from one another. A suitable assay for detecting disruption of cell adhesion is as follows. Bovine pulmonary artery endothelial cells can be harvested by sterile ablation and digestion in 0.1% collagenase (type II; Worthington Enzymes, Freehold, N.J.). The harvested cells are maintained in Dulbecco's minimum essential medium (DMEM) supplemented with 10% fetal calf serum (FCS) and 1% antibiotic-antimycotic at 37° C. and 7% $CO_2$ in air. The cultures are passaged weekly in trypsin-EDTA and seeded onto tissue culture plastic at 20,000 cells/cm$^2$. After one week in culture, which is approximately 3 days after culture confluency is established, the cells are treated (e.g., for 30 minutes) with an siRNA of the invention or a control non-specific siRNA. The cells can be fixed with 1% paraformaldehyde within 24 hours after administration of the siRNA, and the degree of disruption of cell adhesion determined visually by observing retraction of the cells from one another.

RNAi-mediated degradation of target mRNA by an siRNA of the invention can also be evaluated with animal models of neovascularization, such as the retinopathy of prematurity ("ROP") mouse model, the choroidal neovascularization ("CNV") mouse and rat models. For example, areas of neovascularization in a CNV rat can be measured before and after administration of the present siRNA, as in Example 2 below. A reduction in the areas of neovascularization upon administration of the siRNA indicates the down-regulation of ICAM-1 mRNA and a disruption of cell adhesion. Down-regulation of ICAM-1 mRNA and a disruption of cell adhesion is also demonstrated below in the streptozotocin-induced diabetic retinopathy rat model (Example 3), a rat model of VEGF-induced retinal vascular permeability and leukostasis (Example 4), and a rat model of ocular neovascularization induced by corneal/limbal injury (Example 5).

As discussed above, the siRNA of the invention target and cause the RNAi-mediated degradation of human ICAM-1 mRNA, or alternative splice forms, mutants or cognates thereof. Degradation of the target mRNA by the present siRNA reduces the production of a functional gene product from the ICAM-1 gene. Thus, the invention provides a method of inhibiting expression of ICAM-1 in a subject, comprising administering an effective amount of an siRNA of the invention to the subject, such that the target mRNA is degraded.

As the products of the ICAM-1 gene are required for intercellular adhesion or adhesion of cells to the ECM, the invention also provides a method of inhibiting cell adhesion in a subject suffering from cell adhesion or cell adhesion-mediated pathologies. In one embodiment, because ICAM-1-mediated cell adhesion is required for initiating and maintaining angiogenesis, the invention provides a method of inhibiting angiogenesis in a subject by the RNAi-mediated degradation of the target mRNA by the present siRNA. In another embodiment, the invention provides a method of treating a subject for complications arising from type I diabetes, by the RNAi-mediated degradation of the target mRNA by the present siRNA. Preferably, the complications arising from type I diabetes to be treated by the present method are diabetic retinopathy, diabetic neuropathy, diabetic nephropathy, and macrovascular disease (including coronary artery disease, cerebrovascular disease, and peripheral vascular disease).

As used herein, a "subject" includes a human being or non-human animal. Preferably, the subject is a human being.

As used herein, an "effective amount" of the siRNA is an amount sufficient to cause RNAi-mediated degradation of the target mRNA, or an amount sufficient to inhibit the initiation or progression of cell adhesion or cell adhesion-mediated pathologies in a subject.

RNAi-mediated degradation of the target mRNA can be detected by measuring levels of the target mRNA or protein in the cells of a subject, using standard techniques for isolating and quantifying mRNA or protein as described above.

Inhibition of cell adhesion or cell adhesion-mediated pathologies can also be evaluated by measuring the progression of the pathology in the subject, for example by detecting the extent of inflammation, retinopathy, neuropathy, nephropathy or other symptoms characteristic of the disease or disorder for which the subject is being treated.

For example, inhibition of angiogenesis can be evaluated by directly measuring the progress of pathogenic or non-pathogenic angiogenesis in a subject, such as by observing the size of a neovascularized area before and after treatment with the siRNA of the invention. An inhibition of angiogenesis is indicated if the size of the neovascularized area stays the same or is reduced. Techniques for observing and measuring the size of neovascularized areas in a subject are within the skill in the art; for example, areas of choroid neovascularization can be observed by ophthalmoscopy.

Inhibition of angiogenesis can also be inferred through observing a change or reversal in a pathogenic condition associated with the angiogenesis. For example, in AMD, a slowing, halting or reversal of vision loss indicates an inhibition of angiogenesis in the choroid. For tumors, a slowing, halting or reversal of tumor growth, or a slowing or halting of tumor metastasis, indicates an inhibition of angiogenesis at or near the tumor site. Inhibition of non-pathogenic angiogenesis can also be inferred from, for example, fat loss or a reduction in cholesterol levels upon administration of the siRNA of the invention.

The present methods can be used to inhibit angiogenesis which is non-pathogenic; i.e., angiogenesis which results from normal processes in the subject. Examples of non-pathogenic angiogenesis include endometrial neovascularization, and processes involved in the production of fatty tissues or cholesterol. Thus, the invention also provides a method for inhibiting non-pathogenic angiogenesis, e.g., for controlling weight or promoting fat loss, for reducing cholesterol levels, or as an abortifacient.

The present methods can also inhibit angiogenesis which is associated with an angiogenic disease; i.e., a disease in which pathogenicity is associated with inappropriate or uncontrolled angiogenesis. For example, most cancerous solid tumors generate an adequate blood supply for themselves by inducing angiogenesis in and around the tumor site. This tumor-induced angiogenesis is often required for tumor growth, and also allows metastatic cells to enter the bloodstream.

Other angiogenic diseases include diabetic retinopathy and age-related macular degeneration (AMD). These diseases are characterized by the destruction of normal tissue by newly formed blood vessels in the area of neovascularization. For example, in AMD, the choroid is invaded and destroyed by capillaries. The angiogenesis-driven destruction of the choroid in AMD eventually leads to partial or full blindness.

Preferably, an siRNA of the invention is used to inhibit the growth or metastasis of solid tumors associated with cancers; for example breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma; skin cancer (e.g., melanoma), lymphomas and blood cancer.

More preferably, an siRNA of the invention is used to inhibit choroidal neovascularization in age-related macular degeneration.

Particularly preferably, an siRNA of the invention is used to treat complications arising from type I diabetes, such as diabetic retinopathy, diabetic neuropathy, diabetic nephropathy and macrovascular disease.

For treating cell adhesion or cell adhesion mediated pathologies, in particular for treating angiogenic diseases and complications arising from type I diabetes, the siRNA of the invention can be administered to a subject in combination with a pharmaceutical agent which is different from the present siRNA. Alternatively, the siRNA of the invention can be administered to a subject in combination with another therapeutic method designed to treat the pathology. For example, the siRNA of the invention can be administered in combination with therapeutic methods currently employed for treating cancer or preventing tumor metastasis (e.g., radiation therapy, chemotherapy, and surgery). For treating tumors, the siRNA of the invention is preferably administered to a subject in combination with radiation therapy, or in combination with chemotherapeutic agents such as cisplatin, carboplatin, cyclophosphamide, 5-fluorouracil, adriamycin, daunorubicin or tamoxifen.

It is understood that the siRNA of the invention can mediate RNA interference (and thus inhibit cell adhesion) in substoichiometric amounts. Without wishing to be bound by any theory, it is believed that the siRNA of the invention induces the RISC to degrade the target mRNA in a catalytic manner. Thus, compared to standard therapies for cell adhesion or cell adhesion mediated pathologies, significantly less siRNA needs to be administered to the subject to have a therapeutic effect.

One skilled in the art can readily determine an effective amount of the siRNA of the invention to be administered to a given subject, by taking into account factors such as the size and weight of the subject; the extent of disease penetration; the age, health and sex of the subject; the route of administration; and whether the administration is regional or systemic. Generally, an effective amount of the siRNA of the invention comprises an intercellular concentration at the site where intercellular or cell-matrix adhesion is to be inhibited of from about 1 nanomolar (nM) to about 100 nM, preferably from about 2 nM to about 50 nM, more preferably from about 2.5 nM to about 10 nM. It is contemplated that greater or lesser amounts of siRNA can be administered.

In the present methods, the present siRNA can be administered to the subject either as naked siRNA, in conjunction with a delivery reagent, or as a recombinant plasmid or viral vector which expresses the siRNA.

Suitable delivery reagents for administration in conjunction with the present siRNA include the Mirus Transit TKO lipophilic reagent; lipofectin; lipofectamine; cellfectin; or polycations (e.g., polylysine), or liposomes. A preferred delivery reagent is a liposome.

Liposomes can aid in the delivery of the siRNA to a particular tissue, such as retinal or tumor tissue, and can also increase the blood half-life of the siRNA. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), *Ann. Rev. Biophys. Bioeng.* 9: 467; and U.S. Pat. Nos. 4,235,871, 4,501,728, 4,837,028, and 5,019,369, the entire disclosures of which are herein incorporated by reference.

Preferably, liposomes encapsulating the present siRNA comprise a ligand molecule that can target the liposome to cells expressing ICAM-1 at or near the site of angiogenesis or other physiological process involving ICAM-1-mediated cell adhesion, such as a tumor. Cells which express ICAM-1 include endothelial, epithelial, fibroblastic, hematopoietic and tumor cells. Ligands which bind to receptors prevalent in tumor or endothelial cells, such as monoclonal antibodies that bind to tumor antigens or endothelial cell surface antigens, are preferred.

Particularly preferably, the liposomes encapsulating the present siRNA are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes.

Stealth liposomes are known to accumulate in tissues fed by porous or "leaky" microvasculature. Thus, tissue characterized by such microvasculature defects, for example solid tumors, will efficiently accumulate these liposomes; see Gabizon, et al. (1988), *P.N.A.S., USA,* 18: 6949-53. In addition, the reduced uptake by the RES lowers the toxicity of stealth liposomes by preventing significant accumulation in the liver and spleen. Thus, liposomes of the invention that are modified with opsonization-inhibition moieties are particularly suited to deliver the present siRNA to tumor cells.

Opsonization inhibiting moieties suitable for modifying liposomes are preferably water-soluble polymers with a number average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside $GM_1$. Copolymers of PEG, methoxy PEG, or methoxy PPG, or derivatives thereof, are also suitable. In addition, the opsonization inhibiting polymer can include a block copolymer of PEG and either a polyamino acid, polysaccharide, polyamidoamine, polyethyleneamine, or polynucleotide. The opsonization inhibiting polymers can also include natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture such as tetrahydrofuran and water in a 30:12 ratio at 60° C.

Recombinant plasmids which express siRNA of the invention are discussed above. Such recombinant plasmids can also be administered directly or in conjunction with a suitable delivery reagent, including the Mints Transit LT1 lipophilic reagent; lipofectin; lipofectamine; cellfectin; polycations (e.g., polylysine) or liposomes. Recombinant viral vectors which express siRNA of the invention are also discussed above, and methods for delivering such vectors to cells of a subject which are expressing ICAM-1 are within the skill in the art.

The siRNA of the invention can be administered to the subject by any means suitable for delivering the siRNA to cells which express ICAM-1. Cells which express ICAM-1 include non-hematopoietic cells such as vascular endothelial cells, thymic and other epithelial cells, and fibroblasts; and hematopoietic cells such as tissue macrophages, mitogen-stimulated T lymphocyte blasts, and germinal center dendritic cells in tonsils, lymph nodes, and Peyer's patches. One skilled in the art understands that certain cells express ICAM-1 in certain conditions; for example, ICAM-1 is expressed by retinal vascular endothelial cells in ocular neovascular diseases such as diabetic retinopathy or AMD.

Suitable techniques for delivering the siRNA of the invention to ICAM-1-expressing cells include administration of the siRNA to a subject by gene gun, electroporation, nanoparticles, micro-encapsulation, and the like, or by parenteral and enteral administration routes.

Suitable enteral administration routes include oral, rectal, or intranasal delivery.

Suitable parenteral administration routes include intravascular administration (e.g. intravenous bolus injection, intravenous infusion, intra-arterial bolus injection, intra-arterial infusion and catheter instillation into the vasculature); peri- and intra-tissue administration (e.g., peri-tumoral and intra-tumoral injection, intra-retinal injection or subretinal injection); subcutaneous injection or deposition including subcutaneous infusion (such as by osmotic pumps); direct (e.g., topical) application to the area at or near the site of neovascularization, for example by a catheter or other placement device (e.g., a corneal pellet or a suppository, eye-dropper, or an implant comprising a porous, non-porous, or gelatinous material); and inhalation. Suitable placement devices include the ocular implants described in U.S. Pat. Nos. 5,902,598 and 6,375,972, and the biodegradable ocular implants described in U.S. Pat. No. 6,331,313, the entire disclosures of which are herein incorporated by reference. Such ocular implants are available from Control Delivery Systems, Inc. (Watertown, Mass.) and Oculex Pharmaceuticals, Inc. (Sunnyvale, Calif.).

In a preferred embodiment, injections or infusions of the siRNA are given at or near the site of neovascularization. For example, the siRNA of the invention can be delivered to retinal pigment epithelial cells in the eye. Preferably, the siRNA is administered topically to the eye, e.g. in liquid or gel form to the lower eye lid or conjunctival cul-de-sac, as is within the skill in the art (see, e.g., Acheampong A A et al, 2002, *Drug Metabol. and Disposition* 30: 421-429, the entire disclosure of which is herein incorporated by reference).

Typically, the siRNA of the invention is administered topically to the eye in volumes of from about 5 microliters to about 75 microliters, for example from about 7 microliters to about 50 microliters, preferably from about 10 microliters to about 30 microliters. The siRNA of the invention is highly soluble in aqueous solutions, and it is understood that topical instillation in the eye of siRNA in volumes greater than 75 microliters can result in loss of siRNA from the eye through spillage and drainage. Thus, it is preferable to administer a high concentration of siRNA (e.g., about 10 to about 200 mg/ml, or about 100 to about 1000 nM) by topical instillation to the eye in volumes of from about 5 microliters to about 75 microliters.

A particularly preferred parenteral administration route is intraocular administration. It is understood that intraocular administration of the present siRNA can be accomplished by injection or direct (e.g., topical) administration to the eye, as long as the administration route allows the siRNA to enter the eye. In addition to the topical routes of administration to the eye described above, suitable intraocular routes of administration include intravitreal, intraretinal, subretinal, subtenon, peri- and retro-orbital, trans-corneal and trans-scleral administration. Such intraocular administration routes are within the skill in the art; see, e.g., and Acheampong A A et al, 2002, supra; and Bennett et al. (1996), *Hum. Gene Ther.* 7: 1763-1769 and Ambati J et al., 2002, *Progress in Retinal and Eye Res.* 21: 145-151, the entire disclosures of which are herein incorporated by reference.

The siRNA of the invention can be administered in a single dose or in multiple doses. Where the administration of the siRNA of the invention is by infusion, the infusion can be a single sustained dose or can be delivered by multiple infusions. Injection of the siRNA directly into the tissue is at or near the site of neovascularization preferred. Multiple injections of the siRNA into the tissue at or near the site of neovascularization are particularly preferred.

One skilled in the art can also readily determine an appropriate dosage regimen for administering the siRNA of the invention to a given subject. For example, the siRNA can be administered to the subject once, such as by a single injection or deposition at or near the neovascularization site. Alternatively, the siRNA can be administered to a subject multiple times daily or weekly. For example, the siRNA can be administered to a subject once weekly for a period of from about three to about twenty-eight weeks, more preferably from about seven to about ten weeks. In a preferred dosage regimen, the siRNA is injected at or near the site of neovascularization (e.g., intravitreally) once a week for seven weeks. It is understood that periodic administrations of the siRNA of the invention for an indefinite length of time may be necessary for subjects suffering from a chronic neovascularization disease, such as wet AMD or diabetic retinopathy.

Where a dosage regimen comprises multiple administrations, it is understood that the effective amount of siRNA administered to the subject can comprise the total amount of siRNA administered over the entire dosage regimen.

The siRNA of the invention are preferably formulated as pharmaceutical compositions prior to administering to a subject, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in *Remington's Pharmaceutical Science*, 17th ed., Mack Publishing Company, Easton, Pa. (1985), the entire disclosure of which is herein incorporated by reference.

The present pharmaceutical formulations comprise an siRNA of the invention (e.g., 0.1 to 90% by weight), or a physiologically acceptable salt thereof, mixed with a physiologically acceptable carrier medium. Preferred physiologically acceptable carrier media are water, buffered water, saline solutions (e.g., normal saline or balanced saline solutions such as Hank's or Earle's balanced salt solutions), 0.4% saline, 0.3% glycine, hyaluronic acid and the like.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For topical administration to the eye, conventional intraocular delivery reagents can be used. For example, pharmaceutical compositions of the invention for topical intraocular delivery can comprise saline solutions as described above, corneal penetration enhancers, insoluble particles, petrolatum or other gel-based ointments, polymers which undergo a viscosity increase upon instillation in the eye, or mucoadhesive polymers. Preferably, the intraocular delivery reagent increases corneal penetration, or prolongs preocular retention of the siRNA through viscosity effects or by establishing physicochemical interactions with the mucin layer covering the corneal epithelium.

Suitable insoluble particles for topical intraocular delivery include the calcium phosphate particles described in U.S. Pat. No. 6,355,271 of Bell et al., the entire disclosure of which is herein incorporated by reference. Suitable polymers which undergo a viscosity increase upon instillation in the eye include polyethylenepolyoxypropylene block copolymers such as poloxamer 407 (e.g., at a concentration of 25%), cellulose acetophthalate (e.g., at a concentration of 30%), or a low-acetyl gellan gum such as Gelrite® (available from CP Kelco, Wilmington, Del.). Suitable mucoadhesive polymers include hydrocolloids with multiple hydrophilic functional groups such as carboxyl, hydroxyl, amide and/or sulfate groups; for example, hydroxypropylcellulose, polyacrylic acid, high-molecular weight polyethylene glycols (e.g., >200,000 number average molecular weight), dextrans, hyaluronic acid, polygalacturonic acid, and xylocan. Suitable corneal penetration enhancers include cyclodextrins, benzalkonium chloride, polyoxyethylene glycol lauryl ether (e.g., Brij® 35), polyoxyethylene glycol stearyl ether (e.g., Brij® 78), polyoxyethylene glycol oleyl ether (e.g., Brij® 98), ethylene diamine tetraacetic acid (EDTA), digitonin, sodium taurocholate, saponins and polyoxyethylated castor oil such as Cremaphor EL.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of one or more siRNA of the invention. A pharmaceutical composition for aerosol (inhalational) administration can comprise 0.01-20% by weight, preferably 1%-10% by weight, of one or more siRNA of the invention encapsulated in a liposome as described above, and propellant. A carrier can also be included as desired; e.g., lecithin for intranasal delivery.

The invention will now be illustrated with the following non-limiting examples.

Example 1

Inhibition of Human ICAM-1 Expression with siRNAs Targeted to Human ICAM-1 mRNA

Stimulation of ICAM-1 Production in HEK-293 Cells with Cytokines or Hypoxia

The ability of hypoxia or the cytokines tumor necrosis factor alpha (TNF-alpha) and interferon gamma (IFN-gamma) to stimulate production of ICAM-1 in from human embryonic kidney (HEK)-293 cells was evaluated.

HEK-293 cells were cultured in standard growth medium overnight in 24 well plates, at 37° C. with 5% $CO_2$. The cells were then treated separately with 1, 10, 100 or 1000 ng of TNF-alpha or IFN-gamma (R & D Systems, Minneapolis, Minn.), or were made hypoxic by treatment with 100, 200 or 300 micromolar desferrioxamine (Sigma, St. Louis, Mo.). After one or two days treatment with the cytokines or desferrioxamine, the cells were lysed with M-PER Mammalian Protein Extraction reagent (Pierce, Rockford, Ill.). A human ICAM-1 ELISA (R & D systems, Minneapolis, Minn.) was performed on the cell lysates as described in the Quantikine human "sICAM1" ELISA protocol, and the ELISA results were read on an AD340 plate reader (Beckman Coulter).

As shown in FIG. 1, the only conditions which increased the level of human ICAM-1 protein in HEK-293 cells were treatment of the cells with 100 ng/ml TNF-alpha for two days.

Treatment of Stimulated HEK-293 Cells with siRNAs Targeted to Human ICAM-1 mRNA

HEK-293 cells were cultured overnight as in Example 1. Transfections were performed the following day on experimental and control cells, when the cells were approximately 50% confluent. The experimental cells were transfected with 25 nM human ICAM-1 siRNA mixed in calcium phosphate transfection reagent. Control cells were treated with calcium phosphate transfection reagent lacking siRNA, or with 25 nM nonspecific siRNA (EGFP siRNA) in calcium phosphate transfection reagent.

For the experimental cells, ten siRNAs targeted to different locations along the human ICAM-1 mRNA were tested. These siRNAs target the sequences listed in Table 2, and all siRNAs contained 3' TT overhangs on each strand.

TABLE 2

Target Sequences for siRNAs Tested in HEK-293 Cells

| Target Sequence | SEQ ID NO: | siRNA |
|---|---|---|
| AATGCCCAGACATCTGTGTCC | 20 | hICAM1#1 |
| AACAACCGGAAGGTGTATGAA | 29 | hICAM1#2 |
| AACCGGAAGGTGTATGAACTG | 30 | hICAM1#3 |
| AACCTTACCCTACGCTGCCAG | 47 | hICAM1#4 |
| AACGACTCCTTCTCGGCCAAG | 58 | hICAM1#5 |
| AACGTGATTCTGACGAAGCCA | 62 | hICAM1#6 |
| AAGTGTGAGGCCCACCCTAGA | 65 | hICAM1#7 |
| AACTGGACGTGGCCAGAAAAT | 74 | hICAM1#8 |
| AAGTGTCTAAAGGATGGCACT | 80 | hICAM1#9 |
| AACCGCCAGCGGAAGATCAAG | 87 | hICAM1#10 |

Figure 2:
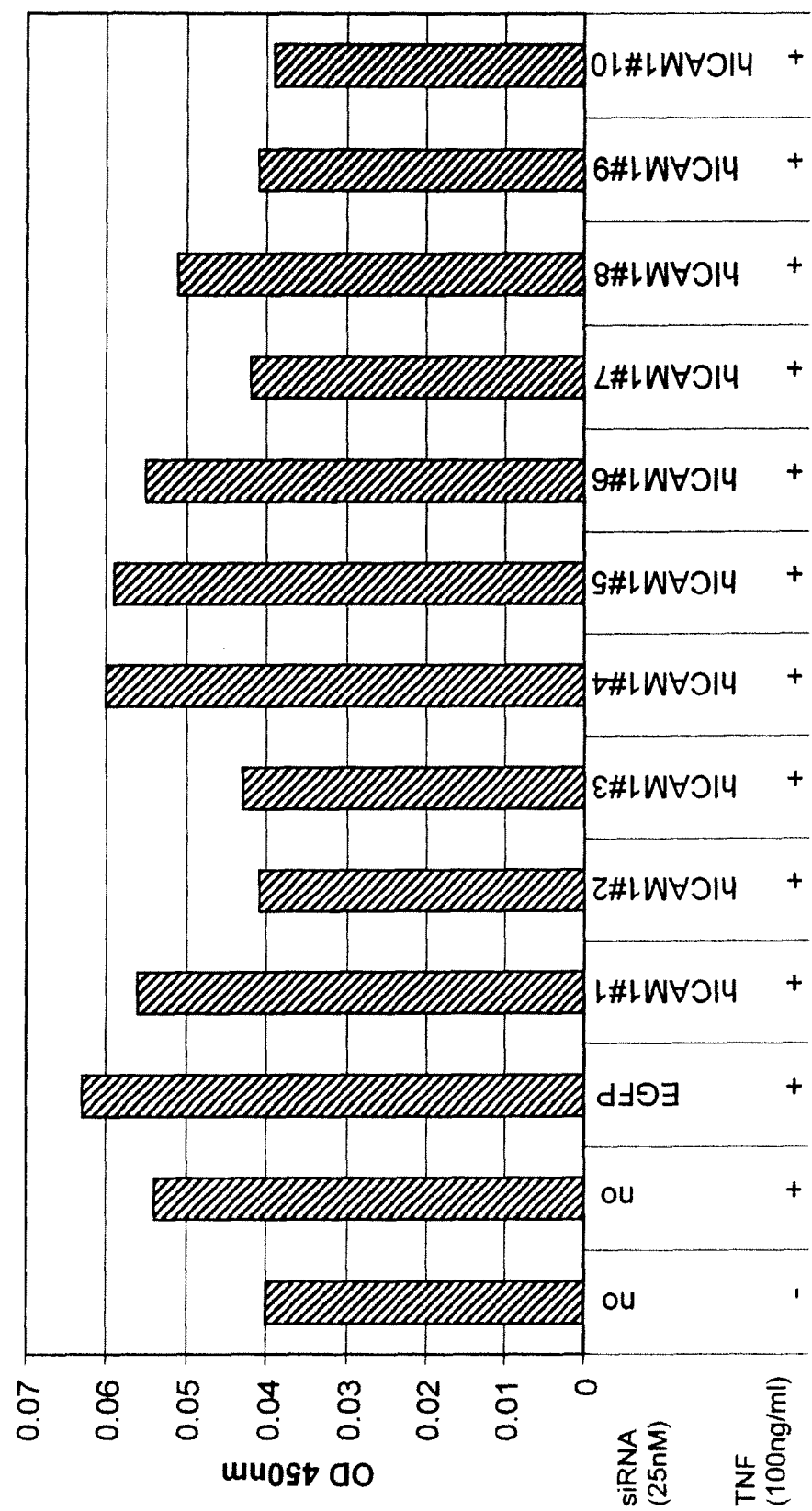
FIG. 2 is a histogram of human ICAM-1 protein concentration, as measured by ELISA at $OD_{450}$ nanometers, in lysates of untreated HEK-293 cells ("−") or HEK-293 cells treated with 100 ng/ml TNF-alpha ("+"). The cells were transfected with no siRNA ("no"), non-specific siRNA ("EGFP") or ten separate siRNAs targeting human ICAM-1 mRNA ("hICAM1#1-10").

Four hours after transfection, production of ICAM-1 was stimulated in the HEK-293 cells by treatment with was TNF-alpha at a final concentration of 100 ng/ml. Forty-eight hours post-transfection, the supernatant was removed from all wells. One group of experimental and control cells were lysed with M-PER Mammalian Protein Extraction reagent (Pierce, Rockford, Ill.). A human ICAM-1 ELISA (R & D systems, Minneapolis, Minn.) was performed on the cell lysates as in Example 1. As shown in FIG. 2, the level of ICAM-1 protein induced in HEK-293 treated with the hICAM1#2, hICAM1#3, hICAM1#7, hICAM1#9 and hICAM1#10 siRNAs was decreased as compared to cells transfected with no siRNA or with a non-specific siRNA.

Figure 3:
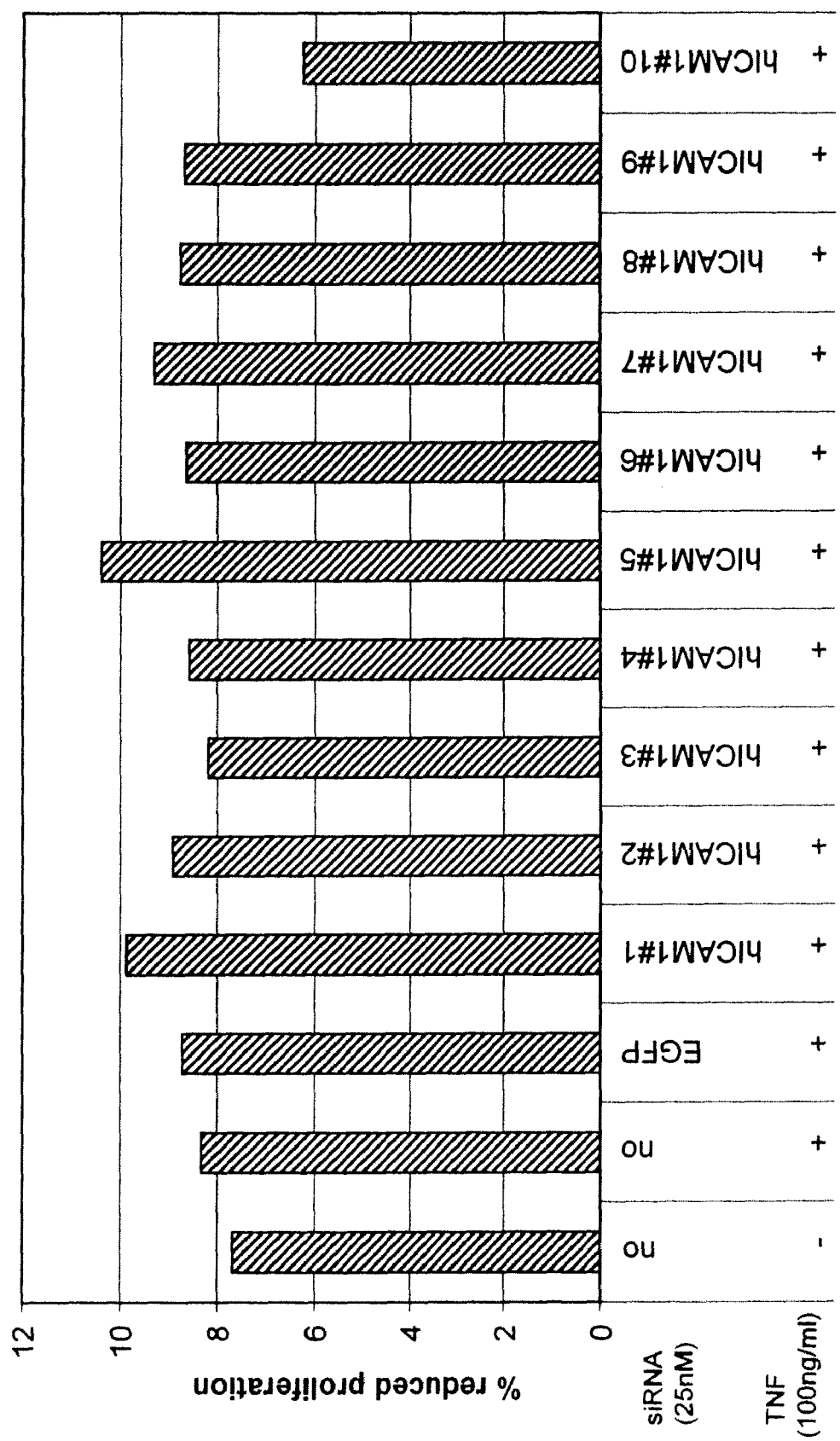
FIG. 3 is a histogram showing cytotoxicity of untreated HEK-293 cells ("−") or HEK-293 cells treated with 100 ng/ml TNF-alpha ("+"). The cells were transfected with no siRNA ("no"), non-specific siRNA ("EGFP") or ten separate siRNAs targeting human ICAM-1 mRNA ("hICAM1#1-10").

A cytotoxicity assay was performed on a second group of experimental and control cells. After removal of the supernatant 48 hours post-transfection as described above, complete growth medium containing 10% AlamarBlue (Biosource, Camarillo, Calif.) was added back to the control and experimental cells, which were incubated at 37° C. with 5% $CO_2$ for 3 hours. Cell proliferation was measured by detecting the color change of medium resulting from cell metabolic activity. This color change was detected on an AD340 plate reader (Beckman Coulter), and the results are given in FIG. 3. As can be seen from FIG. 3, hICAM1#1-9 did not show significant cytotoxicity in the HEK-293 cells. hICAM1#10 produce a slight reduction in HEK-293 cell proliferation as compared to the control cells.

After the cytotoxicity assay was performed, the growth medium containing AlamarBlue was completely removed, and RNA was extracted from the HEK-293 cells with the RNAqueous RNA isolation kit (Ambion, Austin, Tex.) according to the manufacturer's instructions. The levels of human ICAM-1 mRNA in the cells was measured by quantitative reverse transcription-polymerase chain reaction (RT-PCR), using the level of human glyceraldehyde-3-phosphate dehydrogenase (GAPDH) mRNA as an internal standard. The RT-PCR study showed that the production of ICAM-1 induced by TNF-alpha was suppressed by the human ICAM-1 siRNAs at the transcriptional level, as compared to cells transfected with no siRNA or with a non-specific siRNA.

Example 2

Treatment of Streptozotocin-Induced Diabetic Retinopathy with siRNA Targeted to ICAM-1

Vascular leakage and non-perfusion in the retinas of individuals with diabetic retinopathy is spatially and temporally associated with leukocyte stasis. See, e.g., Miyamoto K et al. (1999), *Proc. Nat. Acad. Sci. USA* 96(19):10836-41, the entire disclosure of which is herein incorporated by reference. It is expected that intravitreal injection of siRNA targeted to ICAM-1 will decrease leukocyte stasis, and therefore reduce retinal vascular permeability, in diabetic rats.

Long-Evans rats (approximately 200 g) will be injected with streptozotocin in citrate buffer intravenously after an overnight fast to induce diabetes, as described in Miyamoto K et al. (1999), supra. Long-Evans rats (approximately 200 g) will be injected with citrate buffer alone after an overnight fast as a control. The serum blood sugar will be measured and blood pressure will be recorded daily. Elevated levels of serum blood sugar as compared to control animals are considered diabetic.

Intravitreal injections of siRNA targeted to ICAM-1 will be performed OD in each rat. Non-specific siRNA will be injected as a control OS. The overall group scheme will be as shown in Table 3.

TABLE 3

Overall Group Scheme

| | OD (ICAM-1 siRNA) | OS (non-specific siRNA) |
|---|---|---|
| Diabetic Rat (STZ) | Experimental group | Control |
| Non-diabetic Rat | Control | Control |

At day 7 post treatment, the rats will be subjected to Acridine Orange Leukocyte Fluorography (AOLF), as described in Miyamoto K et al (1999), supra. Briefly, the rats will be anaesthetized, and their pupils dilated with tropicamide. The rats will then be injected intravenously with acridine orange suspended in sterile saline. The fundus of each eye will be observed and imaged with a scanning laser ophthalmoscope (argon blue laser as a light source) for leukocyte stasis. The rats will then be perfused with fluorescein dextran and the eyes will be further imaged. The density of leukocyte stasis will be calculated as a percentage of bright pixels in a 10 disk diameter radius. The density of leukocyte stasis will be used as an endpoint.

Also on day 7, the rats will undergo an isotope dilution technique to quantify vascular leakage, as described in Miyamoto K et al (1999), supra. Briefly, the rats will be injected intravenously with $I^{125}$ in BSA at one time point, and with $I^{131}$ at a second time point. The rats will be sacrificed minutes after the second injection, the retinas will be isolated, and arterial samples will be taken. The retinas and the arterial samples will be analyzed using γ-spectroscopy after correcting for activity in the retinas using a quantitative index of iodine clearance. The measurements will then be normalized for exact dose given, body weight and tissue weight. The corrected quantity of γ activity will be used as a marker of vascular leakage in the retina (second endpoint). It is expected that the γ activity will be decreased in the retinas of the experimental animals, indicating decreased vascular leakage.

Example 3

Treatment of VEGF-Induced Vascular Permeability and Leukostasis with siRNA Targeted to ICAM-1

The presence of VEGF in the eye causes retinal leukostasis that corresponds with increased vascular permeability and capillary non-perfusion in the retina. See, e.g., Miyamoto K et al. (2000), Am. J. Pathol. 156(5):1733-9, the entire disclosure of which is herein incorporated by reference. It is expected that intravitreal injection of siRNA targeted to ICAM-1 will decrease the permeability and leukostasis created by intravitreal injection of VEGF in rats.

Long-Evans rats (approximately 200 g) will be anaesthetized and injected intravitreally with VEGF in buffer OU. siRNA targeted to ICAM-1 will be simultaneously delivered OD to each rat by intravitreal injection. Non-specific siRNA will be injected intravitreally as a control OS. Additional controls will include rats injected with buffer alone (no VEGF). The overall group scheme will be as shown in Table 4.

TABLE 4

Overall Group Scheme

|  | OD (ICAM-1 siRNA) | OS (Non-specific siRNA) |
|---|---|---|
| VEGF | Experimental group | Control |
| Buffer | Control | Control |

At 24 hours post injection the rats are subjected to AOLF and an isotope dilution technique as described in Example 1.

Example 4

Treatment of Neovascularization in Eyes Subjected to Corneal/Limbal Injury with siRNA Targeted to ICAM-1

Injury to the ocular surface can cause the destruction of corneal limbal stem cells. Destruction of these cells induces a VEGF-dependent corneal neovascularization, which can lead to blindness. The VEGF which drives the neovascularization is supplied by neutrophils and monocytes that infiltrate the cornea after injury to the ocular surface. See, e.g., Moromizato Y et al. (2000), Am. J. Pathol. 157(4):1277-81, the entire disclosure of which is herein incorporated by reference in its entirety. It is expected that siRNA targeted to ICAM-1 applied to the cornea after limbal injury will decrease the resultant area of neovascularization of the cornea in mice. The area of neovascularization can be measured directly. Alternatively, a reduction in corneal neovascularization can be inferred from a decrease in the number of VEGF-producing polymorphonuclear cells in the cornea.

Corneal neovascularization will be induced in C57B1/6 by damaging the limbus, as described in Moromizato Y et al., supra. Briefly, the mice will be anaesthetized and sodium hydroxide will be applied to the cornea. The corneal and limbal epithelia will be debrided using a corneal knife OU. siRNA targeted to ICAM-1 will be applied to the corneal surface OD immediately after removal, and 3 times a day for the duration of the study (7 days). Non-specific siRNA will be administered OS with the same dosing regimen as a control.

On days 2, 4 and 7 after debridement of the corneal and limbal epithelia, mice will be evaluated for the degree of corneal neovascularization as described in Moromizato Y et al., supra. Briefly, endothelial-specific, fluorescein-conjugated lectin will be injected intravenously. Thirty minutes after injection, mice will be sacrificed, and the eyes will be harvested and fixed in formalin for 24 hours. Flat mounts of the corneas will be made, and pictures of the corneal flat mounts will be taken under fluorescent microscopy and imported into Openlab software for analysis. Using the Openlab software, threshold level of fluorescence will be set, above which only vessels are seen. The area of fluorescent vessels and the area of the cornea (demarcated by the limbal arcade) will be calculated. The area of vessels will be divided by the total corneal area, and this value will equal the percent neovascular area. The percent neovascular area of the treatment and control groups will be compared.

On days 2, 4 and 7 after debridement of the corneal and limbal epithelia, additional mice will be sacrificed for quantification of corneal polymorphonuclear cells (PMNs) as described in Moromizato Y et al., supra. Briefly, mice will be sacrificed, and the eyes will be harvested and fixed in formalin for 24 hours. After formalin fixation, the enucleated eyes will be embedded in paraffin and sectioned. One paraffin section from each eye which correlates to the corneal anatomical center will be chosen and used for microscopy. The PMNs (identified as multilobulated cells) will be counted on this one section, and the number of PMNs in the sections from the treatment and control groups will be compared.

Example 5

Treatment of Laser-Induced Choroidal Neovascularization with siRNA Targeted to ICAM-1

Laser photocoagulation that ruptures Bruch's membrane will induce choroidal neovascularization (CNV) similar to that seen in wet macular degeneration. It is expected that intravitreal injection of siRNA targeted to ICAM-1 will decrease the area of laser-induced CNV in mice.

CNV will be induced in mice by the procedure described in Sakurai E et al. (2003), *Invest. Ophthalmol. & Visual Sci.* 44(6):2743-9, the entire disclosure of which is herein incorporated by reference. Briefly, C57B1/6 mice will be anaesthetized, and their pupils will be dilated with tropicamide. The retinas of the mice will be laser photocoagulated with one laser spot at the 9, 12, and 3 o'clock positions of each retinal OU. Immediately following laser photocoagulation, inject siRNA targeted to ICAM-1 will be injected intravitreally OD. Non-specific siRNA will be injected intravitreally OS as a control.

Fourteen days after laser photocoagulation, the mice will be sacrificed and retinal flat mounts will be prepared for CNV area quantification as described in Sakurai E et al. (2003), supra. Briefly, the mice will be anaesthetized, the chest will be opened, and the descending aorta will be cross-clamped. The right atrium will then be clipped and fluorescein-labeled dextran will be injected slowly into the left ventricle.

After injection of the fluorescein-labeled dextran, the eyes will be enucleated and fixed in paraformaldehyde for 24 hours. The anterior chamber and retina will then be removed, and a flat mount of each choroid will be prepared for analysis. Choroidal flat mounts will be analyzed by taking a picture of each under fluorescent microscopy, and importing the picture into Openlab software. Using the Openlab software, the area of neovascularization will be outlined and quantified, being sure known laser location is compared to the fluorescent tuft. The neovascular area of the treatment animals will be compared to that of the control animals.

We claim:

1. An isolated siRNA comprising a sense RNA strand and an antisense RNA strand, wherein the sense and an antisense RNA strands form an RNA duplex, and wherein the sense RNA strand comprises a nucleotide sequence substantially identical to a target sequence of about 19 to about 25 contiguous nucleotides in human ICAM-1 mRNA (SEQ ID NO: 1), or an alternative splice form, mutant or cognate thereof, wherein said target sequence comprises SEQ ID NO: 87.

2. The siRNA of claim 1, wherein the cognate of the human ICAM-1 mRNA sequence is mouse ICAM-1 mRNA (SEQ ID NO: 2).

3. The siRNA of claim 1, wherein the sense RNA strand comprises one RNA molecule, and the antisense RNA strand comprises one RNA molecule.

4. The siRNA of claim 1, wherein the sense and antisense RNA strands forming the RNA duplex are covalently linked by a single-stranded hairpin.

5. The siRNA of claim 1, wherein the siRNA further comprises non-nucleotide material.

6. The siRNA of claim 1, wherein the siRNA further comprises an addition, deletion, substitution or alteration of one or more nucleotides.

7. The siRNA of claim 1, wherein the sense and antisense RNA strands are stabilized against nuclease degradation.

8. The siRNA of claim 1, further comprising a 3' overhang.

9. The siRNA of claim 8, wherein the 3' overhang comprises from 1 to about 6 nucleotides.

10. The siRNA of claim 8, wherein the 3' overhang comprises about 2 nucleotides.

11. The siRNA of claim 3 wherein the sense RNA strand comprises a first 3' overhang, and the antisense RNA strand comprises a second 3' overhang.

12. The siRNA of claim 11, wherein the first and second 3' overhangs separately comprise from 1 to about 6 nucleotides.

13. The siRNA of claim 12, wherein the first 3' overhang comprises a dinucleotide and the second 3' overhang comprises a dinucleotide.

14. The siRNA of claim 13, where the dinucleotide comprising the first and second 3' overhangs is dithymidylic acid (TT) or diuridylic acid (uu).

15. The siRNA of claim 8, wherein the 3' overhang is stabilized against nuclease degradation.

16. A retinal endothelial cell comprising the siRNA of claim 1.

17. A recombinant plasmid comprising nucleic acid sequences for expressing an siRNA comprising a sense RNA strand and an antisense RNA strand, wherein the sense and an antisense RNA strands form an RNA duplex, and wherein the sense RNA strand comprises a nucleotide sequence substantially identical to a target sequence of about 19 to about 25 contiguous nucleotides in human ICAM-1 mRNA, or an alternative splice form, mutant or cognate thereof, wherein said target sequence comprises SEQ ID NO: 87.

18. The recombinant plasmid of claim 17, wherein the nucleic acid sequences for expressing the siRNA comprise an inducible or regulatable promoter.

19. The recombinant plasmid of claim 17, wherein the nucleic acid sequences for expressing the siRNA comprise a sense RNA strand coding sequence in operable connection with a polyT termination sequence under the control of a human U6 RNA promoter, and an antisense RNA strand coding sequence in operable connection with a polyT termination sequence under the control of a human U6 RNA promoter.

20. The recombinant plasmid of claim 17, wherein the plasmid comprises a CMV promoter.

21. A recombinant viral vector comprising nucleic acid sequences for expressing an siRNA comprising a sense RNA strand and an antisense RNA strand, wherein the sense and an antisense RNA strands form an RNA duplex, and wherein the sense RNA strand comprises a nucleotide sequence substantially identical to a target sequence of about 19 to about 25 contiguous nucleotides in human ICAM-1 mRNA, or an alternative splice form, mutant or cognate thereof, wherein said target sequence comprises SEQ ID NO: 87.

22. The recombinant viral vector of claim 21, wherein the nucleic acid sequences for expressing the siRNA comprise an inducible or regulatable promoter.

23. The recombinant viral vector of claim 21, wherein the nucleic acid sequences for expressing the siRNA comprise a sense RNA strand coding sequence in operable connection with a polyT termination sequence under the control of a human U6 RNA promoter, and an antisense RNA strand coding sequence in operable connection with a polyT termination sequence under the control of a human U6 RNA promoter.

24. The recombinant viral vector of claim 21, wherein the recombinant viral vector is selected from the group consisting of an adenoviral vector, an adeno-associated viral vector, a lentiviral vector, a retroviral vector, and a herpes virus vector.

25. The recombinant viral vector of claim 21, wherein the recombinant viral vector is pseudotyped with surface proteins from vesicular stomatitis virus, rabies virus, Ebola virus, or Mokola virus.

26. The recombinant viral vector of claim 24, wherein the recombinant viral vector comprises an adeno-associated viral vector.

27. A pharmaceutical composition comprising an siRNA and a pharmaceutically acceptable carrier, wherein the siRNA comprises a sense RNA strand and an antisense RNA strand, wherein the sense and an antisense RNA strands form an RNA duplex, and wherein the sense RNA strand comprises a nucleotide sequence substantially identical to a target sequence of about 19 to about 25 contiguous nucleotides in human ICAM-1 mRNA, or an alternative splice form, mutant or cognate thereof, wherein said target sequence comprises SEQ ID NO: 87.

28. The pharmaceutical composition of claim 27, further comprising lipofectin, lipofectamine, cellfectin, polycations, or liposomes.

29. A pharmaceutical composition comprising the plasmid of claim 17, or a physiologically acceptable salt thereof, and a pharmaceutically acceptable carrier.

30. The pharmaceutical composition of claim 29, further comprising lipofectin, lipofectamine, cellfectin, polycations, or liposomes.

31. A pharmaceutical composition comprising the viral vector of claim 21 and a pharmaceutically acceptable carrier.

32. A method of inhibiting expression of human ICAM-1 mRNA, or an alternative splice form, mutant or cognate thereof, comprising administering to a subject an effective amount of an siRNA comprising a sense RNA strand and an antisense RNA strand, wherein the sense and an antisense RNA strands form an RNA duplex, and wherein the sense RNA strand comprises a nucleotide sequence substantially identical to a target sequence of about 19 to about 25 contiguous nucleotides in human ICAM-1 mRNA, or an alternative splice form, mutant or cognate thereof, such that the human ICAM-1 mRNA, or an alternative splice form, mutant or cognate thereof, is degraded, wherein said target sequence comprises SEQ ID NO: 87.

33. The method of claim 32, wherein the subject is a human being.

34. The method of claim 32, wherein expression of human ICAM-1 mRNA, or an alternative splice form, mutant or cognate thereof is inhibited in one or both eyes of the subject.

35. The method of claim 32, wherein expression of human ICAM-1 mRNA, or an alternative splice form, mutant or cognate thereof is inhibited in retinal pigment epithelial cells of the subject.

36. The method of claim 32, wherein the effective amount of the siRNA is from about 1 nM to about 100 nM.

37. The method of claim 32, wherein the siRNA is administered in conjunction with a delivery reagent.

38. The method of claim 37, wherein the delivery agent is selected from the group consisting of lipofectin, lipofectamine, cellfectin, polycations, and liposomes.

39. The method of claim 38, wherein the delivery agent is a liposome.

40. The method claim 39, wherein the liposome comprises a ligand which targets the liposome to cells expressing ICAM-1.

41. The method of claim 40, wherein the ligand binds to receptors on endothelial, epithelial, fibroblastic, hematopoietic or tumor cells.

42. The method of claim 41, wherein the endothelial cells are retinal vascular epithelial cells.

43. The method of claim 41, wherein the hematopoietic cells are selected from the group consisting of tissue macrophages, mitogen-stimulated T lymphocyte blasts, germinal center dendritic cells in tonsils, germinal center dendritic cells in lymph nodes, and germinal center dendritic cells in Peyer's patches.

44. The method of claim 41, wherein the ligand comprises a monoclonal antibody.

45. The method of claim 39, wherein the liposome is modified with an opsonization-inhibition moiety.

46. The method of claim 45, wherein the opsonization-inhibiting moiety comprises a PEG, PPG, or derivatives thereof.

47. The method of claim 32, wherein the siRNA is expressed from a recombinant plasmid.

48. The method of claim 32, wherein the siRNA is expressed from a recombinant viral vector.

49. The method of claim 48, wherein the recombinant viral vector comprises an adenoviral vector, an adeno-associated viral vector, a lentiviral vector, or a herpes virus vector.

50. The method of claim 49, wherein the recombinant viral vector is a lentiviral vector which is pseudotyped with surface proteins from vesicular stomatitis virus, rabies virus, Ebola virus, or Mokola virus.

51. The method of claim 32, wherein the siRNA is administered by an enteral administration route.

52. The method of claim 51, wherein the enteral administration route is selected form the group consisting of oral, rectal, and intranasal.

53. The method of claim 32, wherein the siRNA is administered by a parenteral administration route.

54. The method of claim 53, wherein the parenteral administration route is selected from the group consisting of intravascular administration, peri- and intra-tissue administration, subcutaneous injection or deposition, subcutaneous infusion, intraocular administration, and direct application at or near the site of neovascularization.

55. The method of claim 54, wherein the intravascular administration is selected from the group consisting of intravenous bolus injection, intravenous infusion, intra-arterial bolus injection, intra-arterial infusion and catheter instillation intro the vasculature.

56. The method of claim 54, wherein the peri- and intra-tissue injection is selected from the group consisting of peritumoral injection, intra-tumoral injection, intra-retinal injection, and subretinal injection.

57. The method of claim 54, wherein the intraocular administration comprises intravitreal, intraretinal, subretinal, subtenon, peri- and retro-orbital, trans-corneal or trans-scleral administration.

58. The method of claim 54, wherein the direct application at or near the site of neovascularization comprises application by catheter, corneal pellet, eye dropper, suppository, an implant comprising a porous material, an implant comprising a non-porous material, or an implant comprising a gelatinous material.

59. The method of claim 58, wherein the site of neovascularization is in the eye, and the direct application at or near the site of neovascularization comprises application by eyedropper.

60. A method of inhibiting cell adhesion or cell adhesion-mediated pathologies in a subject, comprising administering to a subject an effective amount of an siRNA comprising a sense RNA strand and an antisense RNA strand, wherein the sense RNA strand comprises a nucleotide sequence substantially identical to a target sequence of about 19 to about 25 contiguous nucleotides in human ICAM-1 mRNA, or an alternative splice form, mutant or cognate thereof, wherein said target sequence comprises SEQ ID NO: 87.

61. The method of claim 60, wherein the cell adhesion or cell adhesion-mediated pathologies are selected from the group consisting of AIDS-related dementia, allergic conjunctivitis, allergic rhinitis, Alzheimer's disease, angiogenesis, antigen presentation, asthma, atherosclerosis, toxic nephritis, immune-based nephritis, contact dermal hypersensitivity, corneal/limbic injury, type I diabetes, complications arising from type I diabetes, Graves' disease, inflammatory bowel disease, inflammatory lung diseases, inflammatory sequelae of viral infections, inflammatory skin disorders, allograft rejection, immune cell interactions such as T-cell killing, mixed lymphocyte reaction, T-cell mediated B-cell differentiation, meningitis, multiple sclerosis, multiple myeloma, myocarditis, pulmonary fibrosis, reperfusion injury, restensosis, retinitis, rheumatoid arthritis, septic arthritis, stroke, tumor metastasis, and uveitis.

62. The method of claim 61, wherein the inflammatory skin disease is allergic contact dermatitis, fixed drug eruption, lichen planus, or psoriasis.

63. The method of claim 61, wherein the allograft is a renal, liver or bone marrow transplant.

64. The method of claim 62, wherein the angiogenesis is non-pathogenic and is associated with production of fatty tissues, cholesterol production, or endometrial neovascularization.

65. A method of treating an angiogenic disease in a subject, comprising administering to a subject in need of such treatment an effective amount of an siRNA comprising a sense RNA strand and an antisense RNA strand, wherein the sense and an antisense RNA strands form an RNA duplex, and wherein the sense RNA strand comprises a nucleotide sequence substantially identical to a target sequence of about 19 to about 25 contiguous nucleotides in human ICAM-1 mRNA, or an alternative splice form, mutant or cognate thereof, such that angiogenesis associated with the angiogenic disease is inhibited, wherein said target sequence comprises SEQ ID NO: 87.

66. The method of claim 65, wherein the angiogenic disease comprises a cancer.

67. The method of claim 66, wherein the cancer is selected from the group consisting of breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma, skin cancer, lymphoma, and blood cancer.

68. The method of claim 65, wherein the angiogenic disease is selected from the group consisting of diabetic retinopathy and age-related macular degeneration.

69. The method of claim 68, wherein the angiogenic disease is age-related macular degeneration.

70. The method of claim 65, wherein the siRNA is administered in combination with a pharmaceutical agent for treating the angiogenic disease, which pharmaceutical agent is different from the siRNA.

71. The method of claim 70, wherein the angiogenic disease is cancer, and the pharmaceutical agent comprises a chemotherapeutic agent.

72. The method of claim 70, wherein the chemotherapeutic agent is selected from the group consisting of cisplatin, carboplatin, cyclophosphamide, 5-fluorouracil, adriamycin, daunorubicin, and tamoxifen.

73. The method of claim 65, wherein the siRNA is administered to a subject in combination with another therapeutic method designed to treat the angiogenic disease.

74. The method of claim 73, wherein the angiogenic disease is cancer, and the siRNA is administered in combination with radiation therapy, chemotherapy or surgery.

75. A method of treating complications arising from type I diabetes in a subject, comprising administering to a subject in need of such treatment an effective amount of an siRNA comprising a sense RNA strand and an antisense RNA strand, wherein the sense and an antisense RNA strands from an RNA duplex, and wherein the sense RNA strand comprises a nucleotide sequence substantially identical to a target sequence of about 19 to about 25 contiguous nucleotides in human ICAM-1 mRNA, or an alternative splice form, mutant or cognate thereof, wherein said target sequence comprises SEQ ID NO: 87.

76. The method of claim 75, wherein the complications arising from type I diabetes are selected from the group consisting of diabetic retinopathy, diabetic neuropathy, diabetic nephropathy and macrovascular disease.

77. The method of claim 76, wherein the macrovascular disease is coronary artery disease, cerebrovascular disease or peripheral vascular disease.

* * * * *